US008775197B2

(12) United States Patent
Marshall et al.

(10) Patent No.: US 8,775,197 B2
(45) Date of Patent: Jul. 8, 2014

(54) PERSONALIZED HEALTH HISTORY SYSTEM WITH ACCOMMODATION FOR CONSUMER HEALTH TERMINOLOGY

(75) Inventors: Philip Marshall, Portland, PR (US); Brad Bowman, Atlanta, GA (US)

(73) Assignee: WebMD, LLC, New York, NY (US)

( * ) Notice: Subject to any disclaimer, the term of this patent is extended or adjusted under 35 U.S.C. 154(b) by 1827 days.

(21) Appl. No.: 11/219,591

(22) Filed: Sep. 1, 2005

(65) Prior Publication Data

US 2006/0004607 A1 Jan. 5, 2006

Related U.S. Application Data

(63) Continuation-in-part of application No. 10/654,503, filed on Sep. 3, 2003, now Pat. No. 8,612,245, which is a continuation of application No. 09/512,231, filed on Feb. 24, 2000, now abandoned.

(51) Int. Cl.
*G06Q 10/00* (2012.01)
(52) U.S. Cl.
USPC .................................................. 705/2; 705/3
(58) Field of Classification Search
USPC .............................................. 705/2, 3
See application file for complete search history.

(56) References Cited

U.S. PATENT DOCUMENTS

| | | |
|---|---|---|
| 4,315,309 A | 2/1982 | Coli |
| 4,812,994 A | 3/1989 | Taylor et al. |
| 4,858,121 A | 8/1989 | Barber et al. |
| 4,868,376 A | 9/1989 | Lessin et al. |
| 4,882,474 A | 11/1989 | Anderl et al. |
| 4,916,611 A | 4/1990 | Doyle, Jr. et al. |
| 4,949,251 A | 8/1990 | Griffin et al. |
| 4,960,982 A | 10/1990 | Takahira |
| 4,984,272 A | 1/1991 | McIlroy et al. |
| 5,150,409 A | 9/1992 | Elsner |
| 5,241,671 A | 8/1993 | Reed et al. |
| 5,251,152 A | 10/1993 | Notess |
| 5,301,105 A | 4/1994 | Cummings, Jr. |
| 5,301,246 A | 4/1994 | Archibald et al. |
| 5,325,294 A | 6/1994 | Keene |
| 5,327,341 A | 7/1994 | Whalen et al. |
| 5,430,875 A | 7/1995 | Ma |
| 5,465,082 A | 11/1995 | Chaco |
| 5,491,800 A | 2/1996 | Goldsmith et al. |
| 5,517,405 A | 5/1996 | McAndrew et al. |
| 5,550,971 A | 8/1996 | Brunner et al. |
| 5,559,885 A | 9/1996 | Drexler et al. |
| 5,559,888 A | 9/1996 | Jain et al. |

(Continued)

*Primary Examiner* — Lena Najarian
(74) *Attorney, Agent, or Firm* — Wilmer Cutler Pickering Hale and Dorr LLP

(57) ABSTRACT

Personalization of access to health or benefit-related information on a computer network is provided based upon a health history of a user. In one implementation, personal health or benefit-related information about the user is obtaining from the user operating a client computer. The health or benefit-related information includes one or more health or benefit-related terms that each corresponds to a health or benefit-related concept. The health related terms provided by the user are correlated with a health terminology thesaurus that is stored on a computer-readable medium, such as at a server remote from the user client. Each of the health or benefit-related terms is associated with a health or benefit-related concept, which has one or more health or benefit-related works associated therewith. The works associated with health or benefit-related concepts are then made accessible over a computer network to the user.

32 Claims, 21 Drawing Sheets

(56) References Cited

U.S. PATENT DOCUMENTS

| | | | | |
|---|---|---|---|---|
| 5,560,008 A | | 9/1996 | Johnson et al. | |
| 5,572,422 A | | 11/1996 | Nematbakhsh et al. | |
| 5,576,954 A | * | 11/1996 | Driscoll | 1/1 |
| 5,588,148 A | | 12/1996 | Landis et al. | |
| 5,629,981 A | | 5/1997 | Nerlikar | |
| 5,664,109 A | | 9/1997 | Johnson et al. | |
| 5,664,207 A | | 9/1997 | Crumpler et al. | |
| 5,772,585 A | | 6/1998 | Lavin et al. | |
| 5,790,785 A | | 8/1998 | Klug et al. | |
| 5,809,476 A | | 9/1998 | Ryan | |
| 5,815,665 A | | 9/1998 | Teper et al. | |
| 5,827,180 A | | 10/1998 | Goodman | |
| 5,832,488 A | | 11/1998 | Eberhardt | |
| 5,841,970 A | | 11/1998 | Tabuki | |
| 5,845,255 A | | 12/1998 | Mayaud | |
| 5,848,397 A | | 12/1998 | Marsh et al. | |
| 5,857,190 A | | 1/1999 | Brown | |
| 5,862,327 A | | 1/1999 | Kwang et al. | |
| 5,867,799 A | * | 2/1999 | Lang et al. | 1/1 |
| 5,867,821 A | | 2/1999 | Ballantyne et al. | |
| 5,903,889 A | | 5/1999 | De la Huerga et al. | |
| 5,905,884 A | | 5/1999 | Williams | |
| 5,915,240 A | | 6/1999 | Karpf | |
| 5,920,854 A | * | 7/1999 | Kirsch et al. | 1/1 |
| 5,937,387 A | * | 8/1999 | Summerell et al. | 705/2 |
| 5,953,704 A | | 9/1999 | McIlroy et al. | |
| 5,956,722 A | * | 9/1999 | Jacobson et al. | 1/1 |
| 5,960,403 A | | 9/1999 | Brown | |
| 5,966,715 A | | 10/1999 | Sweeney et al. | |
| 5,967,789 A | | 10/1999 | Segel et al. | |
| 5,974,412 A | | 10/1999 | Hazlehurst et al. | |
| 5,978,842 A | | 11/1999 | Noble et al. | |
| 6,006,269 A | | 12/1999 | Phaal | |
| 6,018,619 A | | 1/2000 | Allard et al. | |
| 6,031,818 A | | 2/2000 | Lo et al. | |
| 6,047,327 A | | 4/2000 | Tso et al. | |
| 6,067,552 A | * | 5/2000 | Yu | 715/234 |
| 6,070,160 A | | 5/2000 | Geary | |
| 6,073,106 A | | 6/2000 | Rosen et al. | |
| 6,073,163 A | | 6/2000 | Clark et al. | |
| 6,092,196 A | | 7/2000 | Reiche | |
| 6,112,183 A | | 8/2000 | Swanson et al. | |
| 6,141,759 A | | 10/2000 | Braddy | |
| 6,167,523 A | | 12/2000 | Strong | |
| 6,178,416 B1 | | 1/2001 | Thompson et al. | |
| 6,189,036 B1 | | 2/2001 | Kao | |
| 6,253,228 B1 | | 6/2001 | Ferris et al. | |
| 6,263,330 B1 | | 7/2001 | Bessette | |
| 6,292,796 B1 | | 9/2001 | Drucker et al. | |
| 6,334,778 B1 | | 1/2002 | Brown | |
| 6,347,374 B1 | | 2/2002 | Drake et al. | |
| 6,362,836 B1 | | 3/2002 | Shaw et al. | |
| 6,385,611 B1 | | 5/2002 | Cardona | |
| 6,401,072 B1 | | 6/2002 | Haudenschild et al. | |
| 6,449,598 B1 | * | 9/2002 | Green et al. | 705/2 |
| 6,505,196 B2 | | 1/2003 | Druker et al. | |
| 6,826,696 B1 | | 11/2004 | Chawala et al. | |
| 7,020,618 B1 | | 3/2006 | Ward | |
| 2001/0021910 A1 | | 9/2001 | Goldstein | |
| 2002/0032772 A1 | * | 3/2002 | Olstad et al. | 709/224 |
| 2003/0195877 A1 | * | 10/2003 | Ford et al. | 707/3 |
| 2007/0226204 A1 | * | 9/2007 | Feldman | 707/5 |

* cited by examiner

| CLINICAL MEDICAL TERM OR TERMS | LAY MEDICAL TERM | CUI |
|---|---|---|
| GUARDING OF THE ABDOMEN-INVOLUNTARY | ABDOMEN SENSITIVE TO TOUCH | C0238547 |
| NIPPLE DISCHARGE, ABNORMAL | ABNORMAL NIPPLE DISCHARGE | 00149741 |
| ADRENALIN-TEST | ADRENALIN LEVEL | C0201998 |
| AMINOPHYLLINE, SERUM | AMINOPHYLLINE LEVEL | C0002575 |
| AMITRIPTYLINE, SERUM | AMITRIPTYLINE LEVEL | C0202316 |
| AMMONIA - TEST | AMMONIA LEVEL | 00201879 |
| SALICYLATE, SERUM | ASPIRIN LEVEL | 00202463 |
| CONGENITAL BAND SYNDROME | BABY BANDS | C0220724 |
| URINATION, BED WETTING | BED WETTING | 00014394 |
| OROPHARYNX LESION BIOPSY | BIOPSY OF THROAT | 00192211 |
| PERIODS, MENSTRUAL - BLEEDING BETWEEN | BLEEDING BETWEEN MENSTRUAL PERIODS | 00302811 |
| EAR DISCHARGES/BLEEDING | BLEEDING FROM EAR | 00271412 |
| HOG (QUALITATIVE - SERUM) | BLOOD HCG LEVEL | 00430064 |
| HEMOGLOBIN, SERUM | BLOOD HEMOGLOBIN LEVEL | 00523685 |
| LEAD - SERUM | BLOOD LEAD LEVEL | 00524167 |
| LITHIUM, SERUM | BLOOD LITHIUM LEVEL | 00337452 |
| BORN WITH AN OPTIC DISC ABNORMALITY | BORN WITH AN ABNORMAL OPTIC NERVE | 00521571 |
| TACHYPNEA | BREATHING FAST | C0231835 |
| BACKBONE FRACTURE | BROKEN BACK | 00080179 |
| METACARPAL FRACTURE | BROKEN METACARPAL | 00272677 |
| SACRUM/ COCCYX FRACTURE | BROKEN TAILBONE | 00149860 |
| MONOPLEGIA OF LOWER EXTREMITY | CAN'T MOVE LEG | 00154702 |
| DYSURIA | PAIN WITH URINATION | 00028961 |
| VISION, NIGHT BLINDNESS | CAN'T SEE AT NIGHT | 00028077 |
| INABILITY TO SLEEP | CAN'T SLEEP | 00021603 |
| SMELL, IMPAIRED | CAN'T SMELL | 00481703 |
| MEDIAN NERVE RELEASE | CARPAL TUNNEL SURGERY | C0196576 |
| HOARSENESS OR CHANGING VOICE | CHANGING VOICE | 00518179 |
| CHEST LACERATION | CHEST CUT | C0432951 |
| HICCUPS, CHRONIC | CHRONIC HICCUPS | 00019521 |
| CHRONIC PAIN AND FATIGUE CONDITION | CHRONIC PAIN | 00150055 |
| DIURETIC | WATER PILL | C0033231 |
| HYDROXYZINE INJECTION | CORTISONE SHOT | C0010137 |
| COMPUTERIZED TOMOGRAPHY OF ORBIT | CT OF EYE SOCKET | 00202754 |
| CXR | CHEST XRAY | 00202783 |
| FRACTURE | BROKEN | 00016658 |
| DIABETES MELLITUS | SUGAR DISEASE | 00011849 |

Fig. 5

CUI Parent Search

Show Family ▼

Search Type: ⊙ Condition ○ Medication

Type in Cui to display relations then click on search button.

[C0018799]   (search)    Add a Relationship

Condition relationships for CUI:
C0018799 Heart Disease [CUI]

Parents:
- X0182783 Disorder of blood vessels of thorax [CUI] ✗
- ●●X0021558 Disease of thorax [CUI] ✗
- ●●●X0026569 Disease of trunk [CUI]
- ●●C0042373 Vascular Disease [CUI]
- ●●●C0007222 Diseases of the Heart and Surrounding Blood Vessels [CUI]

Children:
X0223665 Acute heart disease [CUI] ✗
C0564747 Acute/subacute carditis [CUI] ✗
X0230493 Anomalous bands of heart [CUI] ✗
C0340520 Athlete's heart [CUI] ✗
C0161816 Cardiac complication [CUI] ✗
C0558373 Cardiac disease in pregnancy [CUI] ✗
C0574106 Cardiac glycogen phosphorylase kinase deficiency [CUI] ✗
C0155715 Cardiac septal defect, acquired [CUI] ✗
C0027049 Cardiomyopathy [CUI] ✗
X0214507 Chronic heart disease [CUI] ✗
C0010054 Coronary Artery Disease [CUI] ✗
C0265122 Diseases of the Heart Sac, Unspecified [CUI] ✗
X0212581 Disorder of cardiac function [CUI] ✗
X0213881 Endocardial disease [CUI] ✗

Fig. 6

| 107 | | | | |
|---|---|---|---|---|
| CUI 1 | CONCEPT | RELATED CONCEPTS | TYPE | WEIGHT COEFFICIENT | RELATED WORKS |
| CUI 2 | CONCEPT | RELATED CONCEPTS | TYPE | WEIGHT COEFFICIENT | RELATED WORKS |
| ... | ... | ... | ... | ... | ... |
| CUI N | CONCEPT | RELATED CONCEPTS | TYPE | WEIGHT COEFFICIENT | RELATED WORKS |

Fig. 7

| CUI | Name | Type | Total Weight | Last Updated |
|---|---|---|---|---|
| X0311332 | Morphine | Allergy | 5 | 05/31/2003 14:09:42 |
| | XD108121 Analgesics | | | |
| | XD110172 Analgesics, Narcotics | | | |
| | XD114588 Nervous System (except Autonomic) | | | |
| C0018772 | HEARING IMPAIRED | Condition | 8 | 05/31/2003 14:09:42 |
| | CD011053 Deafness | | | |
| | XD214548 Hearing Disorder | | | |
| | XD220080 Finding of ability to hear | | | |
| | XD011849 Sensory nervous system finding | | | |
| | XD020919 Auditory observations | | | |
| | XD213816 Ear and auditory finding | | | |
| C0020443 | Elevated Cholesterol in Blood | Condition | 8 | 05/31/2003 14:09:42 |
| | CD02D471 Elevated Blood Fats | | | |
| | CD342831 Disorder of lipoprotein storage and metabolism | | | |
| | CD268195 Disorder of lipoprotein and lipid metabolism, NOS | | | |
| C0020490 | Farsighted | Condition | 8 | 05/31/2003 14:09:42 |
| | CD271180 Eye Sight Refraction and Accomodation Disorder | | | |
| | CD024951 Refractive Errors | | | |
| | CD042790 Vision Disorders | | | |

Fig. 8

| CUI | Total Weight | Term |
|---|---|---|
| X0020919 | 8 | Auditory observations |
| C0011053 | 8 | Deafness |
| X0021560 | 8 | Disease of abdomen |
| C0009373 | 8 | Disease of Colon |
| C0266806 | 8 | Disease of digestive organ, NOS |
| X0222359 | 8 | Disease of gastrointestinal tract |
| X0213865 | 8 | Disease of large intestine |
| C0266805 | 8 | Disease of lower digestive tract, NOS |
| C0268195 | 8 | Disorder of lipoprotein and lipid metabolism, NOS |
| C0342830 | 8 | Disorder of lipoprotein storage and metabolism |
| X0213836 | 8 | Ear and auditory finding |
| C0020473 | 8 | Elevated Blood Fats |
| C0020443 | 8 | Elevated Cholesterol in Blood |
| C0271180 | 8 | Eye Sight Refraction and Accomodation Disorder |
| C0020490 | 8 | Farsighted |
| X0220080 | 8 | Finding of ability to hear |
| C0016807 | 8 | Functional intestinal disorder, unspecified |
| X0214548 | 8 | Hearing Disorder |
| C0018772 | 8 | HEARING IMPAIRED |
| C0021831 | 8 | Intestinal Diseases |
| C0022104 | 8 | Irritable Bowel Syndrome |
| C0034951 | 8 | Refractive Errors |
| X0013849 | 8 | Sensory nervous system finding |
| C0042790 | 8 | Vision Disorders |

| Page Score | Tool | CUI | Mult | Targeting (gender, min months, max months, cui1, cui2, cui3, xcui1) Your age is 422 months. |
|---|---|---|---|---|
| 25 | Prostate Health Center | WC018891 | 5 | Male,216,2000,WC018891=at Risk for Prostate Cancer,-,-, |
| 24 | Cholesterol Center | C0020443 | 3 | both,216,2000,C0020443=Elevated Cholesterol in Blood,-,-, |
| 24 | Eye Health Center | C0034951 | 3 | both,216,2000,C0034951=Refractive Errors,-,-, |
| 16 | Irritable Bowel Syndrome Center | C0022104 | 2 | both,216,2000,C0022104=Irritable Bowel Syndrome,-,-, |
| 15 | Cholesterol Center | C0521974 | 3 | both,216,2000,C0521974=High fat diet,-,-, |
| 9 | Fitness Center | C0031812 | 3 | both,216,2000,C0031812=Fitness,-,-, |
| 9 | LEAP | C0015259 | 3 | both,216,2000,C0015259=Exercise,-,-, |
| 9 | LEAP | C0031812 | 3 | both,216,2000,C0031812=Fitness,-,-, |
| 9 | Men's Health Center |  | 3 | Male,216,2000,-,-,-, |
| 6 | LEAP |  | 2 | both,216,2000,-,-,-, |
| 3 | Drug Interaction Checker |  | 1 | both,216,2000,-,-,-, |
| 3 | Stress Center |  | 1 | both,216,2000,-,-,-, |
| 3 | Topics A-Z |  | 1 | both,0,2000,-,-,-, |
| 3 | Trackers |  | 1 | both,0,2000,-,-,-, |
| 0.999996 | Erectile Dysfunction Center | C0021116 | 3 | Male,216,2000,C0021116=Erectile Dysfunction,-,-, |

Fig. 17

| Raw Weight | Time factor | Page Score | Article | Cui | Mult | Targeting (gender, min months, max months, cui2, cui3, xcui1) Your age is 422 months. |
|---|---|---|---|---|---|---|
| 25 | 0.832000 | 20.8 | Few Concerned Despite High Stroke Risk | WC018894 | 5 | both,216,2000,WC018894=at Risk for Stroke,- |
| 24 | 0.800000 | 19.2 | Many More Americans Need Cholesterol-Lowering Treatment | C0020443 | 3 | both,216,2000,C0020443=Elevated Cholesterol,-,- |
| 32 | 0.552000 | 17.664 | Drug Combo Improves Cholesterol Levels | C0020443 | 4 | both,216,2000,C0020443=Elevated Cholesterol,-,- |
| 20 | 0.800000 | 16 | Many More Americans Need Cholesterol-Lowering Treatment | WC018877 | 4 | both,216,2000,WC018877=at Risk for Coronary Disease,-,- |
| 20 | 0.768000 | 15.36 | Heart Scans No Help in Lowering Risk | WC018877 | 4 | both,216,2000,WC018877=at Risk for Coronary Disease,-,- |
| 24 | 0.608000 | 14.592 | Cholesterol Control Alternatives | C0020443 | 3 | both,216,2000,C0020443=Elevated Cholesterol,-,- |

Search Results

Your search on "Trouble Breathing" produced the following results:

■ Topic: Asthma
  Or go to Exercise Induced Asthma, COPD, Allergies, Coughing,
       Pneumonia, or try an Advanced Seach

Search Results

⊞ Statistics (1)
⊟ Overview (3)

Asthma Overview, source, publication date, abstract text
  Asthma Overview2, source, publication date, abstract text
  Execrcise Induced Asthma Overview, source, publication...
  Trouble breathing Overview, source, publication...
  Childhood Asthma Overview, source, publication...

⊞ Causes (3)
⊞ Symptoms (4)
⊞ Risk factors (5)
⊞ Tests & diagnosis (10)
⊞ Prevention (1)
⊞ Treatments (19)

Related Tools
- Asthma Assessment
- Peak Flow Tracker
- LEAP Fitness Program

Related Benefits
- Benefit Content link1
- Benefit Content link2
- Benefit Content link3

Advanced Search

| Trouble Breathing | Advanced Options:
                     ⦿ Best matches
                     More matches:
                     ○ with all of these words
                     ○ with any of these words

Your search for "diabetes" produced the following results:

Topic: Diabetes (Diabetes Mellitus)

*From WebMD*

Diabetes Condition Center
Diabetes Assessment and Care Plan

Medical reference (148)
- Diabetes Overview, Healthwise
- Diabetes Basics, National Library of Medicine
- Understanding Diabetes -- the Basics
...more Definition
Overview (3)
- From The Cleveland Clinic: Frequently Asked Questions About Diabetes, Cleveland Clinic
- From the Cleveland Clinic: What Is Diabetes
- Understanding Diabetes -- the Basics
...more News (32)
- Diabetes + Hypertension = Silent Stroke, WebMD
  Silent strokes are also powerful predictors of deadly strokes. And a new study finds they're common in diabetes patients who have high blood pressure.
- Diabetes May Raise Birth Defect Risk, WebMD
  Congenital heart defects are five times more likely in babies born to women with diabetes, a study shows.
- Macho Attitude May Add to Diabetes Deaths, WebMD
  The rise in diabetes deaths in the U.S. may be partly due to the macho attitudes of young men.
...more Clinical Trials (1)
- Diabetes Mellitus, Insulin-Dependent

- Diabetes - Type I

---

Topic Navigator

- ⊞ Diseases and Conditions
  - ⊞ Glandular Disorders
    - ⊞ Diabetes
      ▲ Diabetes Mellitus
        - ⊞ Causes
        - ⊞ Symptoms
        - ⊞ Risk Factors
        - ⊞ Tests
        - ⊞ Prevention
        - ⊟ Treatments
          - ⊞ Prescription Drugs
          - ⊞ Alternative Health
          - ⊞ Devices
          - ⊞ Surgery
        - ⊞ Related to ...
        - ⊞ Celebrities

Fig. 22

PERSONALIZED HEALTH HISTORY SYSTEM WITH ACCOMMODATION FOR CONSUMER HEALTH TERMINOLOGY

CROSS-REFERENCE TO THE RELATED APPLICATIONS

This application is a continuation-in-part of U.S. application Ser. No. 10/654,503, filed on Sep. 3, 2003 now U.S. Pat. No. 8,612,245, which is a continuation of U.S. application Ser. No. 09/512,231, filed on Feb. 24, 2000, now abandoned.

FIELD OF THE INVENTION

The present invention relates to providing personalized access to content that is available over a computer network and, in particular, to providing health or benefit-related works that are accurately personalized according to personal health information about the user, including health information that is described in lay medical terminology.

BACKGROUND OF THE INVENTION

Consumer health information is growing in importance and popularity, with computer networks such as the Internet providing a growing share of the information. It is estimated that health issues are addressed at tens of thousands of online sites with potentially millions of pages of health or benefit-related works. With a general lack of clinical and editorial standards for health or benefit-related works, lay consumers without specific medical training, and even trained medical professionals, can have relatively little success in finding desired or relevant information among such vast resources.

Moreover, given the extremely personal nature of health, most individuals have minimal interest in browsing materials that have no relevance to their health or the health of their families. Yet most of the health information available at conventional network (e.g., Internet) sites or portals addresses only general topics. Such information seldom has any particular relevance to individual users. Accordingly, there is a need for an improved way of obtaining relevant or personalized health or benefit-related works from computer networks such as the Internet.

Conventional network (e.g., Internet) systems employ a variety of personalization processes that at least minimally personalize a network site for different visitors or users. The personalization provided by many such processes is relatively simplistic and provides personalization only to the extent of a small number of personalization options. These conventional personalization processes include Greetings, which can be as simple as providing a "welcome sign" that informs the user of the state of a single condition, such as, "Hello you've got mail;" Pick Lists, which allow users to select from predetermined lists of news categories, horoscopes, sports scores, etc.; Keywords, codes or symbols, which can be referenced by entering keywords such as zip codes for local weather forecasts or stock ticker symbols for stock quotes; Demographic/traffic analysis, which is usually derived from a log file which indicates a user's name, email address, zip code, and Internet Service Provider information; Comparison methods, which use data provided by other users to highlight similarities and differences among users; and Collaborative processes, which select works based on the preferences of others who are in some way similar to the user.

Personalization processes in use today, including the use of demographics and pick-lists, are inadequate for the vast amounts of health or benefit-related information and the relatively narrow interests of many users. Pick Lists are useful, when the possible selections number fewer than several (e.g., 4 or 5) dozens. However, health related works can be usefully categorized among hundreds or thousands of distinct topics. As a consequence, conventional health-related network sites that employ Pick Lists for personalization typically provide relatively few selections that each cover broad areas of information. Such broad coverage areas render such personalization ineffective for the specific health or benefit-related information desired by many users.

SUMMARY OF THE INVENTION

The present invention provides systems and methods for accessing health or benefit-related works by the user. In one implementation of a system, the personal health or benefit-related information may be obtained from a user, obtained from other information sources or systems, or both. The personal health information may relate to health conditions, which may include medical diagnoses like diabetes, high blood pressure, pneumonia, or pregnancy, or any current or past health problems like poor vision, chronic joint pain, cancer, or alcoholism. The health information could also or alternatively relate to medications, health risks, allergies, tests, vaccinations, surgeries or procedures, etc. that affect or have affected the health of the user or that are a part of the user's health history. The benefit information may relate to the user's medical plan, their drug benefit, and also or alternatively their prior utilization of health care services or benefits.

The system filters from the obtained health or benefit-related information several health or benefit-related terms or codes that correspond to one or more health or benefit-related concepts stored in a health terminology thesaurus. Some of these terms may be clinical medical terms or codes, which are typically used by the medical professionals, and others may be lay medical terms. Each of the health or benefit-related terms may be associated with a single identifier that uniquely identifies a corresponding health or benefit-related concept. Each identifier has associated with it one or more terms corresponding to a common health or benefit-related concept.

Concept-specific identifiers may also be used to identify health or benefit-related works that are accessible over a computer network. The health or benefit-related works may include, for example, health news, product and service information, information relating to the health plan benefits or other benefits available to the person, disease information, medication information, articles, movie and audio clips, treatises, advertisements and other health or benefit-related content. Each health or benefit-related work has associated therewith one or more concept-specific identifiers that are used to describe the content or subject matter of the work.

Concept-specific identifiers may also be assigned to health or benefit-related works to identify individually or in combination the attributes of an appropriate target population that would benefit from receiving the health or benefit-related work. Personalization of the health or benefit-related work then matches the concept-specific identifiers associated with the user with the concept-specific identifiers used to describe the appropriate target population that would benefit from receiving the work.

In one implementation of the system, several health or benefit-related concepts may be in taxonomic or semantic relationship with each other. The taxonomically related concepts have a parent/child relationship. Such relationships may be derived, for example, from existing professional healthcare vocabularies, including SNOMED, Medical Subject Headings, and International Classification of Diseases. Thus, for example, taxonomic relationships allow the term "type 2 sugar disease", which equates to the concept of "adult-onset diabetes mellitus", to be related as a child concept to "diabetes mellitus", which in turn is a child concept of "diabetes", which in turn is a child concept to "endocrine and glandular disorders". This then allows an article written simply about "Diabetes" to find all those who would benefit from this information, including those who are described as having "type 2 sugar disease."

In contrast, the semantically related concepts have functional relationships, which comprise "treatment of", "causes of", "test for", and other functional relationships. The semantically related concepts allow users interested in "Diabetes" to have access, for example, to articles written about current diabetes medications, advertisement of new diabetes detection and treatment techniques and clinics where such treatment is offered, as well as other diabetes-related works. Additional benefit of the semantically related concepts is that using functional relationships users are can conduct narrowly targeted, and thus very efficient, searches among the wealth of available health or benefit-related works.

In another implementation, the system may maintain a user profile for each user. The user profile can be implemented as a data structure stored in a non-volatile memory. The user profile may contain the health or benefit-related concepts associated with personal medical terms provided by the user, gathered from other information sources, or both. For each health or benefit-related concept, the user profile may contain the URLs or memory addresses for the associated health or benefit-related works. Furthermore, the health or benefit-related concepts may be organized in the user profile in a taxonomic order to reflect their taxonomic relationship. In addition, health or benefit-related concepts having semantic relationships may be organized in the user profile in a semantic order. The profile may be periodically updated to reflect actions taken by the user, including opening articles or tools.

In one implementation of the system, each item in the user profile may have a weight coefficient assigned thereto, which may depend on source and relevance of the item. A weight coefficient associated with a health or benefit-related concept may indicate relevance of the concept to the user. The value of such weight coefficient may be higher for those concepts in which the user expresses a greater interest. Such determination may be made, for example, by observing the number of times that the user accessed health or benefit-related works associated with a particular concept. Similarly, the value of the weight coefficient may decrease if the user expresses very little or no interest in a particular health or benefit-related concept, and may eventually result in the removal of such health or benefit-related concept from the user profile. The value of such weight coefficient may also differ for concepts in the user profile based upon the source of the concept. For example, a health condition concept originating as a diagnosis code from a doctor's office may get a higher weight coefficient than the same concept that is self-reported from the user or inferred from the concepts associated with the health or benefit-related works accessed by the user.

The weight coefficients may also be associated with health or benefit-related works. In this case, a weight coefficient may indicate one or more of the following criteria: popularity of the health or benefit-related work, age of the health or benefit-related work, scope of the health or benefit-related work, and relevance of the health or benefit-related work. So, for example, for a user who identified himself as having "type 2 sugar disease", a recently published article on the subject of "adult-onset diabetes mellitus" will be give a higher weight coefficient than an old article on general subject of "diabetes." In addition, the value of the weight coefficient may be adjusted to reflect the popularity of the article among other users having similar interests. Thus, if the frequency of access to a particular article increases, the weight coefficient of the article will also increase. Furthermore, if the article is deemed to be important by the medical community, the weight coefficient assigned to the article will also be very high.

The weight coefficients may also be associated with the concepts assigned to health or benefit-related works. In this case, a weight coefficient may indicate the degree to which the concept describes the subject matter of the work. For example, if a news article is focused on the topic of diabetes, the concept of diabetes would be weighted higher than in another article where diabetes is mentioned only in passing.

The weight coefficients may also be associated with the concepts used to identify attributes of an appropriate target population, either individually or in aggregate. In this case, a weight coefficient may indicate the degree to which the health or benefit-related work would be useful or beneficial to a member of the target population. For example, an article describing new findings of a cure for stomach ulcers may be targeted to a profile attribute of stomach ulcers with a high weighting, while a lower weighting would be used to target the same article to someone with heartburn as a profile attribute.

Since it is impracticable, and often impossible, to display all health or benefit-related works associated with the heath-related concepts that may be of interest to the user, the weight coefficients of the health or benefit-related concepts tied to the health or benefit-related works combined with the weight coefficients of the health or benefit-related concepts tied to the attributes of the user may be used to effectively prioritize works having the greatest relevance to the user. For example, in one implementation of the system, the weight coefficient of the health or benefit-related concept may be multiplied by the weight coefficient of the health or benefit-related works associated with that concept to generate a page scores for all works in the user profile. Page scores are then ranked and only works with the highest page scores are displayed to the user. As the weight coefficients of the health or benefit-related concepts and the associated health or benefit-related works change, the page scores will change and the works provided to the user will also dynamically change.

In one embodiment of the invention, a computer-implemented method for providing health or benefit-related works to a user comprises: associating at least one health or benefit-related term provided by the user with one or more health or benefit-related concepts, wherein two or more health or benefit-related concepts are at least in a taxonomic relationship or a semantic relationship with each other; identifying one or more health or benefit-related works associated with the one or more health or benefit-related concepts; displaying to the user the health or benefit-related concepts associated with the at least one provided health or benefit-related term, wherein the health or benefit-related concepts having taxonomic relationship are displayed in taxonomic order and the health or benefit-related concepts having semantic relationship are displayed in the semantic order; and providing to the user a computer network access to the health or benefit-related works associated with the displayed health or benefit-related concepts.

In another embodiment, a computer-implemented method for providing health or benefit-related works to a user comprises: obtaining from the user personal health or benefit-related information comprising one or more health or benefit-related terms; associating one or more of the obtained health or benefit-related term with one or more health or benefit-related concepts; associating a weight coefficient with each health or benefit-related concept, wherein a weight coefficient determines relevance of the associated health or benefit-related concept to the user; identifying one or more health or benefit-related works associated with the health or benefit-related concept, wherein a health or benefit-related work and/or its associated concepts have a weight coefficient assigned thereto; and providing to the user computer network access to one or more of the identified health or benefit-related works based on a function of the weight coefficient of the health or benefit-related concept and the weight coefficients of the associated health or benefit-related works.

In yet another embodiment, a computer-implemented method for providing health or benefit-related works to a user comprises: retrieving a user profile data structure, wherein the user profile data structure comprises one or more health or benefit-related concepts and weight coefficients associated therewith for indicating relevance of the health or benefit-related concept to the user; identifying one or more health or benefit-related works associated with one or more health or benefit-related concepts, wherein a health or benefit-related work and/or its associated concepts have a weight coefficient assigned thereto; and providing to the user computer network access to one or more of the identified health or benefit-related works based on a function of the weight coefficient of the health or benefit-related concept and the weight coefficient of the health or benefit-related concepts assigned to the health or benefit-related work.

In one embodiment, a system for providing health or benefit-related works to a user comprises: a computer-readable medium having a user profile data structure stored thereon, wherein the user profile data structure comprises: (i) one or more health or benefit-related concepts, wherein a health or benefit-related concept has weight coefficient associated therewith indicating relevance of the health or benefit-related concept to the user, and (ii) links to one or more health or benefit-related works associated with one or more health or benefit-related concepts, wherein such concepts have weight coefficients assigned thereto; and a processor operable to access the user profile data structure and to provide to the user a computer network access to one or more of the health or benefit-related works based on a function of the weight coefficient of the health or benefit-related concept and the weight coefficient of the associated health or benefit-related work.

In another embodiment, the invention includes computer software for providing health or benefit-related works to the user, the computer software comprising: instructions for defining a user profile data structure comprising one or more health or benefit-related concepts and weight coefficients associated therewith for indicating relevance of the health or benefit-related concept to the user; instructions for identifying one or more health or benefit-related works associated with one or more health or benefit-related concepts, wherein a health or benefit-related work and/or its associated concepts has a weight coefficient assigned thereto; and instructions for providing to the user computer network access to one or more of the identified health or benefit-related works based on a function of the weight coefficient of the health or benefit-related concept and the weight coefficient of the health or benefit-related work.

In yet another embodiment, a computer-implemented method for providing health or benefit-related works to a user comprises: associating a health or benefit-related work with one or more health or benefit-related concepts; assigning a weight coefficient to the health or benefit-related work based at least on one of the following criteria: popularity of the health or benefit-related work, age of the health or benefit-related work, scope of the health or benefit-related work; assigning one or more user criteria to the health or benefit-related work, wherein the criteria comprises on or more of the following: age of the targeted user, gender of the targeted user; and providing to the user a computer network access to the health or benefit-related work.

In sum, the present invention provides systems and methods for accessing health or benefit-related information while accommodating the particular interests of both professional and lay users and the vast amounts of and conflicting terminology in health or benefit-related information. In contrast, the conventional personalization processes are inadequate for the particularized interests of users in combination with the vast and complex resources of health or benefit-related information.

BRIEF DESCRIPTION OF THE DRAWINGS

FIG. 5 is a table of exemplary health concepts and corresponding terms.

FIG. 6 is an illustration of the taxonomically related concepts.

FIG. 7 is a schematic diagram of a user profile data structure.

FIGS. 8 and 9 are exemplary embodiments of the user profile data structure.

FIGS. 16 and 17 are two exemplary embodiments of user profile data structures.

FIG. 18 is an exemplary personalized search results.

FIG. 20 is an exemplary works indexing tool.

FIG. 22 is an illustration of the semantically related concepts.

DETAILED DESCRIPTION OF THE INVENTIONS

Figure 1:
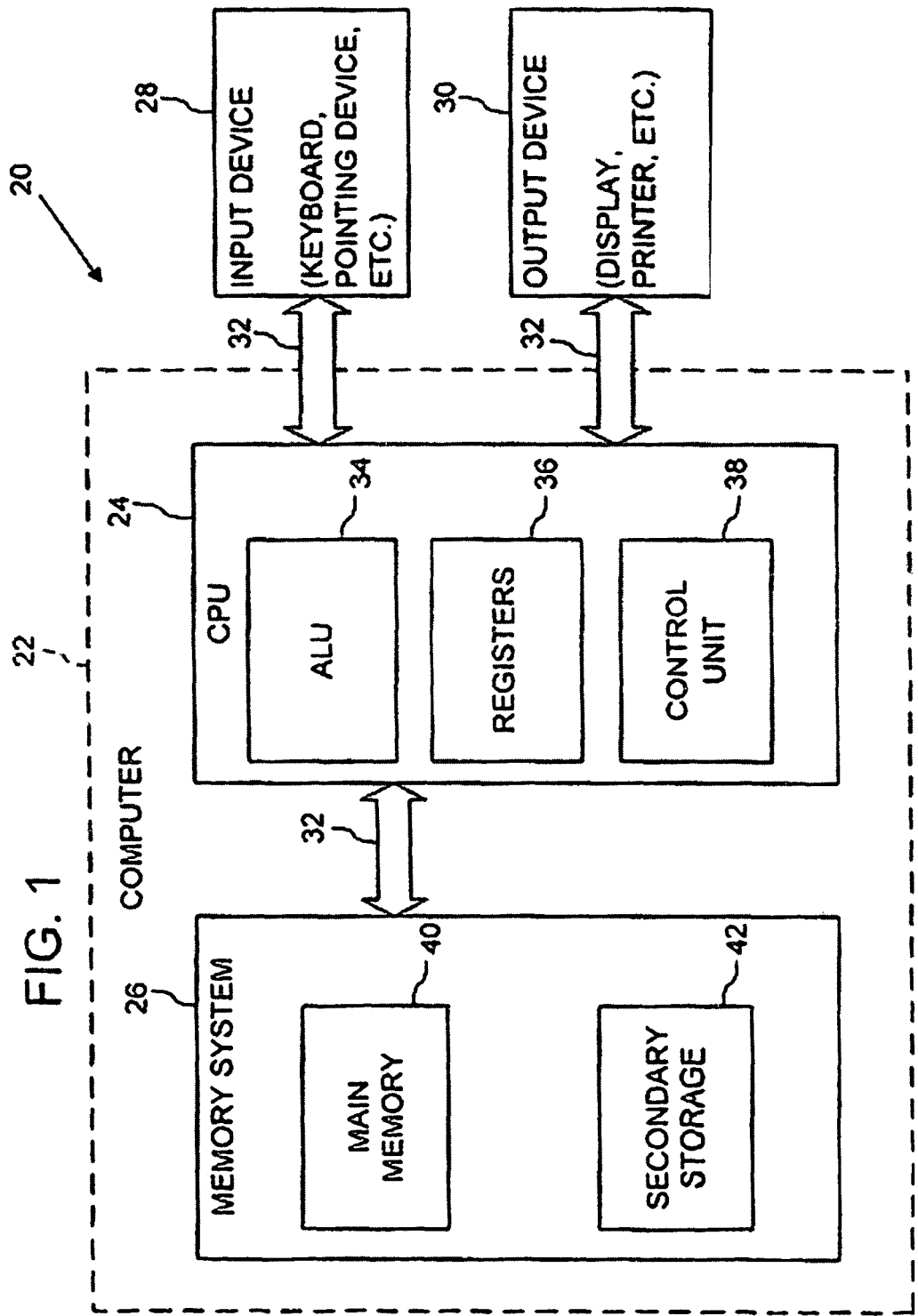
FIG. 1 is a block diagram of an implementation of computer system of the present invention.

FIG. 1 illustrates an operating environment for an embodiment of the present invention as a computer system 20 with a computer 22 that comprises at least one high speed processing unit (CPU) 24 in conjunction with a memory system 26, an input device 28, and an output device 30. These elements are interconnected by at least one bus structure 32.

The illustrated CPU 24 is of familiar design and includes an ALU 34 for performing computations, a collection of registers 36 for temporary storage of data and instructions, and a control unit 38 for controlling operation of the system 20. The CPU 24 may be a processor having any of a variety of architectures including Alpha from Digital, IMPS from MIPS Technology, NEC, IDT, Siemens, and others, x86 from Intel and others, including Cyrix, AMD, and Nexgen, and the PowerPC from IBM and Motorola.

The memory system 26 generally includes high-speed main memory 40 in the form of a medium such as random access memory (RAM) and read only memory (ROM) semiconductor devices, and secondary storage 42 in the form of long term storage mediums such as floppy disks, hard disks, tape, CD-ROM, flash memory, etc. and other devices that store data using electrical, magnetic, optical or other recording media. The main memory 40 also can include video display memory for displaying images through a display device. Those skilled in the art will recognize that the memory 26 can comprise a variety of alternative components having a variety of storage capacities.

The input and output devices 28 and also are familiar. The input device 28 can comprise a keyboard, a mouse, a physical transducer (e.g., a microphone), etc. The output device can comprise a display, a printer, a transducer (e.g., a speaker), etc. Some devices, such as a network interface or a modem, can be used as input and/or output devices.

As is familiar to those skilled in the art, the computer system further includes an operating system and at least one application program. The operating system is the set of software which controls the computer system's operation and the allocation of resources. The application program is the set of software that performs a task desired by the user, using computer resources made available through the operating system. Both are resident in the illustrated memory system 26.

In accordance with the practices of persons skilled in the art of computer programming, the present invention is described below with reference to acts and symbolic representations of operations that are performed by computer system 20, unless indicated otherwise. Such acts and operations are sometimes referred to as being computer-executed and may be associated with the operating system or the application program as appropriate. It will be appreciated that the acts and symbolically represented operations include the manipulation by the CPU 24 of electrical signals representing data bits which causes a resulting transformation or reduction of the electrical signal representation, and the maintenance of data bits at memory locations in memory system 26 to thereby reconfigure or otherwise alter the computer system's operation, as well as other processing of signals. The memory locations where data bits are maintained are physical locations that have particular electrical, magnetic, or optical properties corresponding to the data bits.

Figure 2:
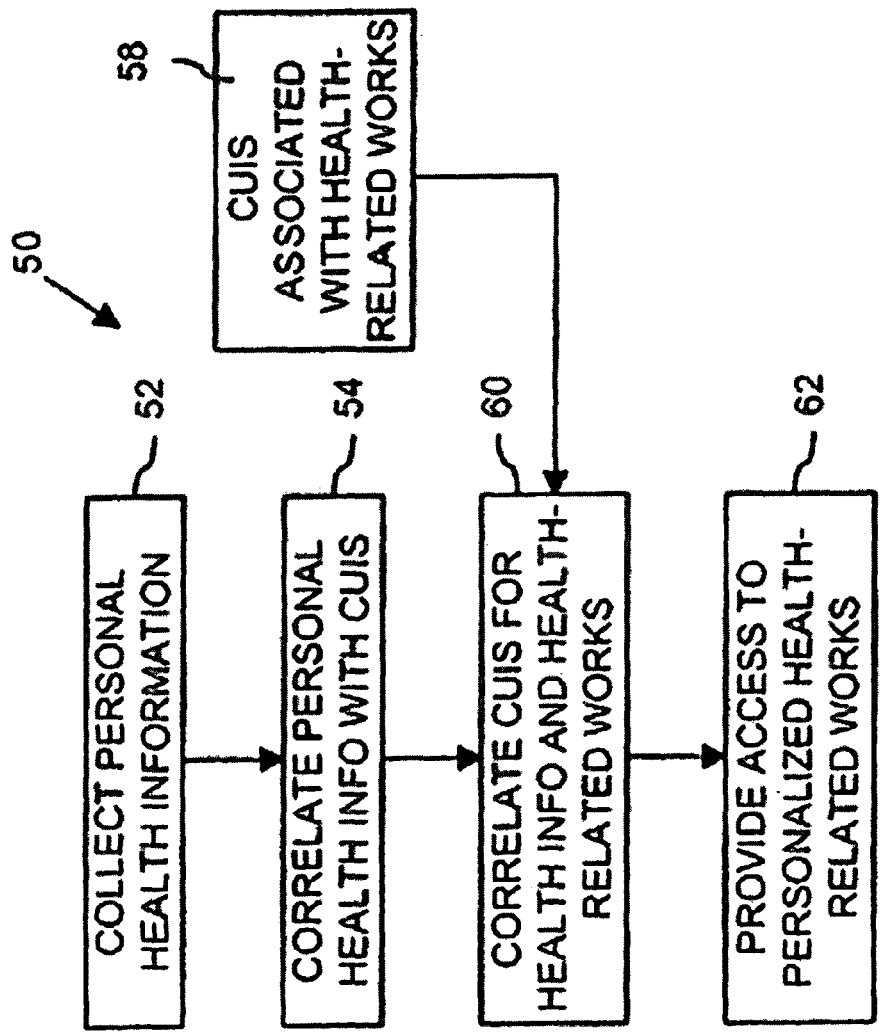
FIG. 2 is a flow diagram of one embodiment of a health history personalization process.

With reference to FIG. 2, a flow diagram of a health history personalization process 50 in accordance with one embodiment of the present invention is illustrated. The process 50 may be used to personalizing health or benefit-related works that is accessible via a computer network by a user. The user commonly being a lay individual without specific medical training. The computer network may be private or public and may be a local area network or a wide area network. In one implementation, health history personalization process 50 operates and access to the health or benefit-related works are provided to the user over the Internet.

Process block 52 indicates that personal health information is collected about the user. The personal health information may relate to health conditions, which may include medical diagnoses like diabetes, high blood pressure, pneumonia, or pregnancy, or any current or past health problem like poor vision, chronic joint pain, cancer, or alcoholism.

Alternatively, the health information could relate to allergies, tests, medications, health risks, vaccinations, surgeries or procedures, etc. that affect or have affected the health of the user or that are a part of the user's health history. For purposes of explanation, the following description is made with reference to the health information relating to health conditions. It will be appreciated that the description is similarly applicable to other types of health information, including information relating to allergies, tests, vaccinations, surgeries or procedures, etc.

Process block 54 indicates that the personal health information are correlated with predefined concept-specific identifiers. Each concept uniquely identifies a predefined health or benefit-related concept (e.g., a health condition). The concept-specific identifiers provide standardized identification of the predefined health or benefit-related concepts independent of traditional variations between lay medical and clinical medical terminology for health conditions, as described below in greater detail. In one implementation, the concept-specific identifiers are in the form of alpha-numeric segments (e.g., 8 characters each). Alternatively, numeric or alphabetic segments could be used.

The concept-specific identifiers are based on core medical concepts, enabling multiple synonyms and related terms to be mapped to the same concept-specific identifier or code. For example, "hyperpeisis," "elevated systolic pressure," "high blood pressure," "hypertensive vascular disease" and "high blood" are all used in consumer and professional circles to describe the same thing: high blood pressure. Accordingly, all these terms would be mapped or associated with a single concept-specific identifier.

Process block 58 indicates that one or more concept-specific identifiers are associated with each of many health or benefit-related works (e.g., health news, product and service information, disease information, medication information, and other health or benefit-related content that are available over the network) that relate to the predefined health or benefit-related concepts corresponding to the concept-specific identifiers. The associations between the health or benefit-related works and the concept-specific identifiers are maintained in a database as a data structure on a computer-readable medium.

In addition to the association of concept-specific identifiers pertaining to the subject of the health related works, a combination of concept-specific identifiers is associated with the health related works to identify the appropriate populations of users for whom the health or benefit-related work are most appropriate. Additive concept-specific identifiers are used to identify populations of appropriate users, such as male, age 40-60, history of prostate cancer, on the medicine Lupron, and on the medicine Aspirin. Exclusion of concepts from the target population of users is also performed, such as the above criteria, but excluding users who are on the medicine Proscar.

As another example for how the system can utilize a combination of concept-specific identifiers and excluded concept-specific identifiers to define populations of appropriate recipients for health or benefit-related works, the association of subject-based concept-specific identifiers to a news article entitled "Exercise found to reduce the risk for breast cancer" will result in the concept-specific identifiers for breast cancer, breast cancer prevention, and exercise. This article then is also indexed with a combination of concept-specific identifiers (additive and/or excluded) for which the article is most appropriate. For example, the above mentioned article would be "targeted" to women between the ages of and 70 who are at risk for breast cancer but who have not had a history of breast cancer.

Process block 60 indicates that the concept-specific identifiers for the personal health information collected about the user are correlated with the concept-specific identifiers of health or benefit-related works available over the computer network to identify health or benefit-related works that is personalized for the user.

Process block 62 indicates that access to the personalized health-related works is provided to the user. It will be appreciated that the access to the works may be provided to the user in a number of ways. For example, the personalized health or benefit-related works may be provided as personalized hyperlinks that are selectable by the user or the works themselves may be provided directly to the user. The access to the personalized health or benefit-related works may be provided to the user in several ways. For example, the access to the works may be "pushed" to the user without a specific request by the user for the information, but rather, based upon the personal health information provided by the user. As another example, the access to the information may be provided to the user in response to a specific request or search by the user.

Exemplary concept-specific identifiers and corresponding predefined health or benefit-related concepts or terms for several health conditions are listed below in FIG. 5. The relationship between each concept-specific identifier and the corresponding health or benefit-related term or terms forms a data structure that is stored in a computer-readable medium and includes a concept-specific identifier (e.g., alphanumeric) and one or more associated health or benefit-related terms. The data structure allows uniform identification of health or benefit-related concepts despite a variety of lay medical terms and clinical medical terms being in use. The listing of concepts in FIG. 5 is not exhaustive of the health condition medical terms to which the concept-specific identifiers may be applied.

The concept-specific identifiers and corresponding predefined health or benefit-related terms form a health terminology thesaurus that is stored on a computer-readable medium and provides the concept-specific identifiers based upon the health or benefit-related terms. The WebMD thesaurus incorporates terminology from many health-related vocabularies, including the Systematized Nomenclature of Medicine (SNOMED) promulgated by the College of American Pathologists and the International Classification of Diseases: 9th revision, Clinical Modification, promulgated by the Health Care Financing Administration, as well as the Consumer Health Terminology® created by WellMed, Inc (now WebMD, Inc.).

To improve search of and access to health or benefit-related works, in one implementation of the system, several health or benefit-related concepts may be organized based on their taxonomic and/or semantic relationships. Taxonomic relationship is the classification of concepts in an ordered system that indicates their natural relationships. One example of a taxonomic relationship between several concepts is shown in FIG. 6. In the illustrated taxonomic relationship, one or more concepts organized into families, in which several concepts form parent/child relationships. Such relationships may be derived, for example, from existing professional healthcare vocabularies, including SNOMED, Medical Subject Headings, and International Classification of Diseases. Thus, for example, in a taxonomic relationship "adult-onset diabetes mellitus" is a child concept of "diabetes mellitus", which in turn is a child concept of "diabetes", which in turn is a child concept to "endocrine and glandular disorders".

Taxonomic organization of concepts allows the system to search several related concepts and retrieve health or benefit-related works that may not be associated with one but not with another related concept. Thus, an article about narrow concept of type 2 sugar disease may be retrieved in response to the search for a broader concept of diabetes.

In another implementation of the system, several concepts may be in semantic (or functional) relationship. One example of a semantic relationship between several concepts is shown in FIG. 22. Several concepts can be related semantically using their functional relationships, such as "treatment of", "causes of", "test for", etc. The semantically related concepts allow users interested in "diabetes" to have access, for example, to articles written about current diabetes medications, advertisement of new diabetes detection and treatment techniques and clinics where such treatment is offered, as well as other diabetes-related works. Additional benefit of the semantically related concepts is that using functional relationships users are can conduct narrowly targeted, and thus very efficient, searches among the wealth of available health or benefit-related works.

Figure 3:
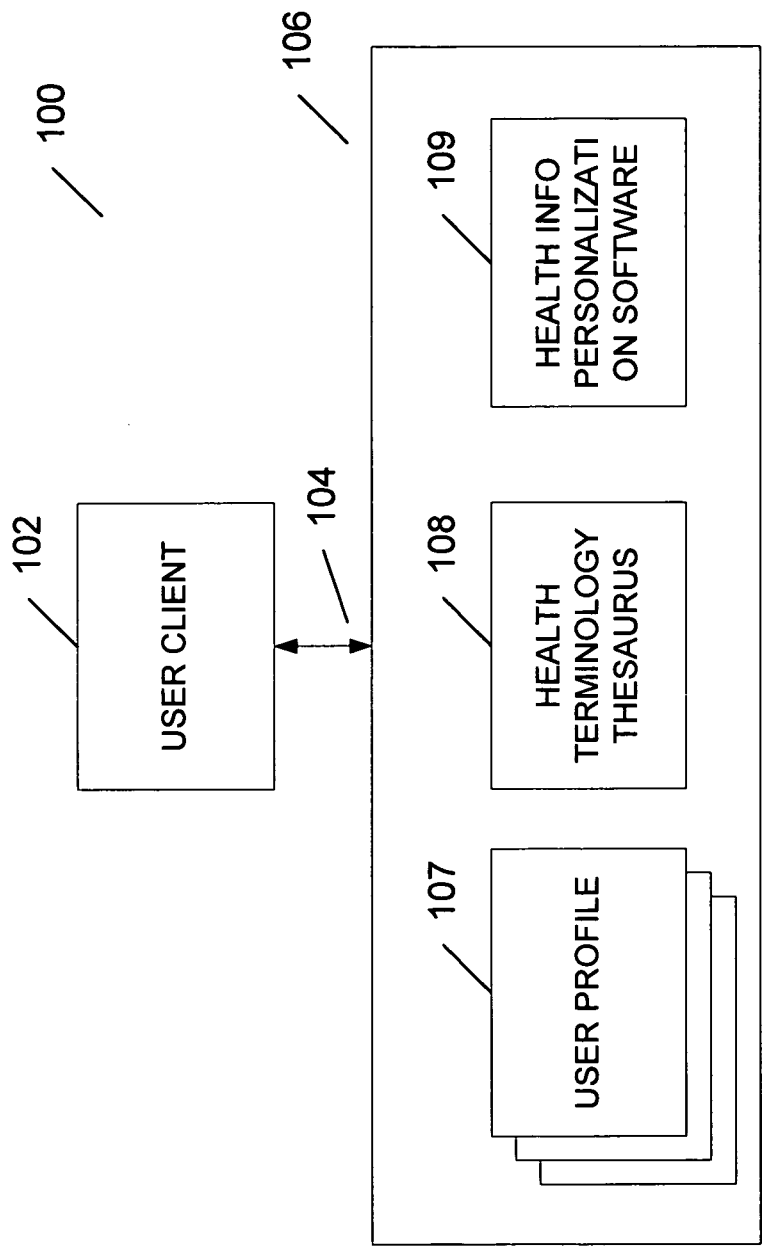
FIG. 3 is a block diagram of one implementation of a health history personalization computer system.

FIG. 3 is a block diagram of one implementation of a health history personalization computer system 100, in accordance with the present invention. The system 100 includes a user client 102 that communicates over a computer network 104 with a health history personalization server 106. Server 106 may be implemented as one or more server computers. In the case of multiple server computers, they may be local to each other or may be remote from each other and in communication via a computer network. User client 102 may be implemented as, for example, an interactive document or page that is accessible by the user at a client computer with conventional browser software.

In one implementation of the system, health history personalization server 106 stores a health terminology thesaurus 108 that correlates health terminology or codes with concept-specific identifiers. Health history personalization server 106 may also include health information personalization software 109 that cooperates with user client 102 for identifying the concept-specific identifiers that correspond to personal health information (e.g., health conditions) specified by the user. Furthermore, server 106 may also maintain user health profile data structures that contain personal health information provided by the user along with the associated health or benefit-related concepts.

Figure 4:
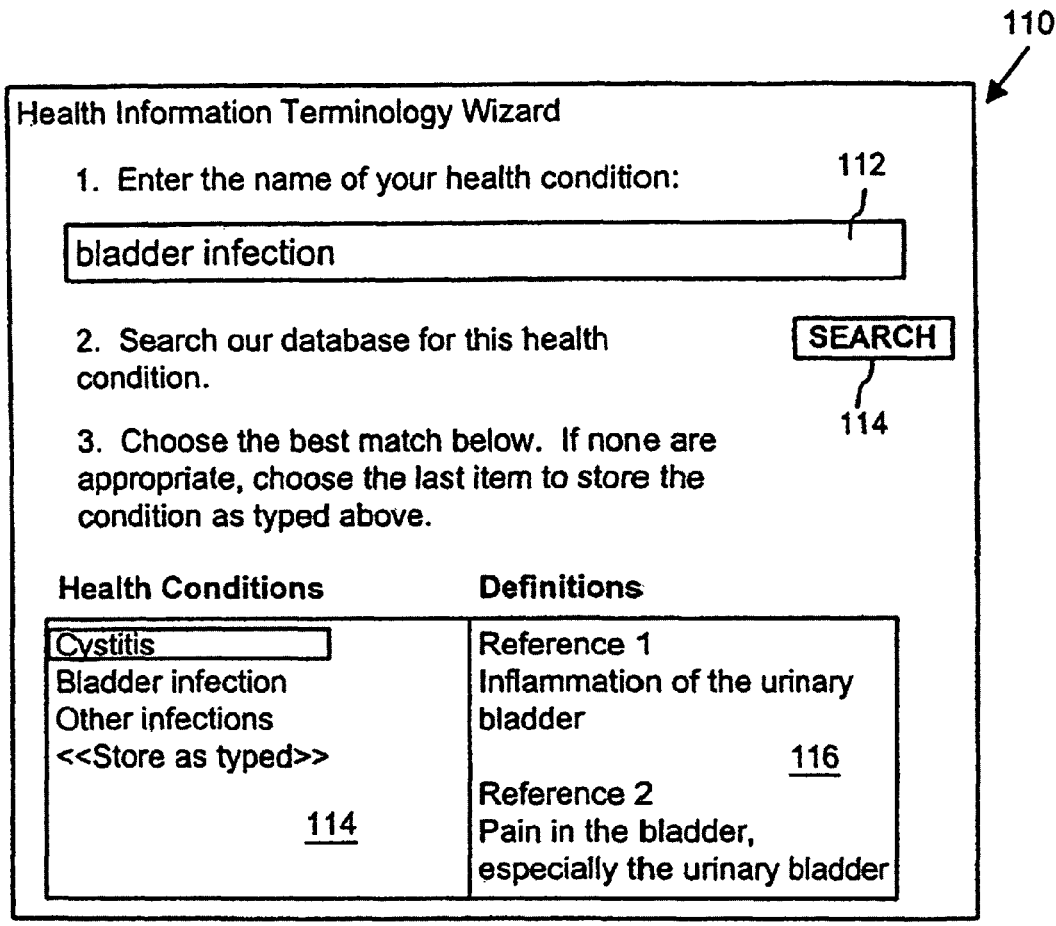
FIG. 4 is a diagram of a health information terminology wizard user interface.

FIG. 4 illustrates a health information terminology wizard user interface 110 that is rendered on a display screen for the user by user client 102. Health information terminology wizard user interface 110 assists a user in providing personal health information to health history personalization computer system 100.

User interface 110 includes a health information (e.g., health condition) entry pane 112 in which the user is prompted to enter a current or past health condition. A graphical control 114 allows the user to commence a search of health terminology thesaurus 108 for terms that are related or correspond to the health condition terminology the user entered into entry pane 112. In one implementation, the commencing of the search results in the health condition terminology entered by the user being transmitted over network 104 to health history personalization server 106 where thesaurus 108 is stored.

Any health terms that health information personalization software 109 identifies in thesaurus 108 as corresponding or relating to the information entered by the user are returned for display in a health terminology (e.g., health conditions) pane 114 of user interface 110. A prompt instructs the user to select one of the returned health terms that best corresponds to the user's health condition. Alternatively, the user may select an instruction to store the health information (e.g., health condition) as entered in entry pane 112. In one optional implementation, user interface 106 includes a definitions pane 116 in which text definitions may be provided for health terms selected by the user from health terminology pane 114 (e.g., cystitis in the illustration of FIG. 4).

Health information personalization software 109 further includes a health terminology spell checking component that checks the spelling of terms entered by the user. In the event of apparent misspellings or unrecognized terms, server 106 returns to health terminology pane 114 one or more suggested correct spellings.

Health history personalization server 106 correlates a concept-specific identifier with the health term selected by the user as corresponding to the user's health condition, unless the user selects the instruction to store the health information (e.g., health condition) as typed in entry pane 112 rather than one of the returned matches. The concept-specific identifier may be stored at server 106 with identifying information regarding the user in a user profile. When submitting a query in the entry pane 112, users may use a word related to the desired result. For example, the user may enter "heart" in the health conditions entry pane 112 to retrieve a list of health conditions having to do with the heart. Similarly, the user may enter "diabetes" to find all health conditions related to diabetes.

Also stored at server 106 are a listing of health or benefit-related works that is available over the network and concept-specific identifiers indicative of the subject matter of the works. For example, server 106 could store a link or a network address for a news article entitled "Gene Identified As Cause Of Skin Disease" having associated with it the subject concepts of Xeroderma Pigmentosa (concept C0043345), skin cancer (concept 00007114), and genetic research (concept C0243064).

Server 106 correlates the user's personal health information (e.g., health conditions) with the corresponding health or benefit-related works. Server 106 identifies works having the same concept-specific identifiers as those associated with the user's personal health information. For example, the news article entitled "Gene Identified As Cause Of Skin Disease" could be correlated with users who have Xeroderma Pigmentosa (concept C0043345), and users with skin cancer (concept 00007114). Links to the news article could be provided to both groups of users either in response to searches they conduct related to the specified topics, or the links may be delivered to the users automatically as a "push" of potentially relevant information identified at server 106.

Figure 15:
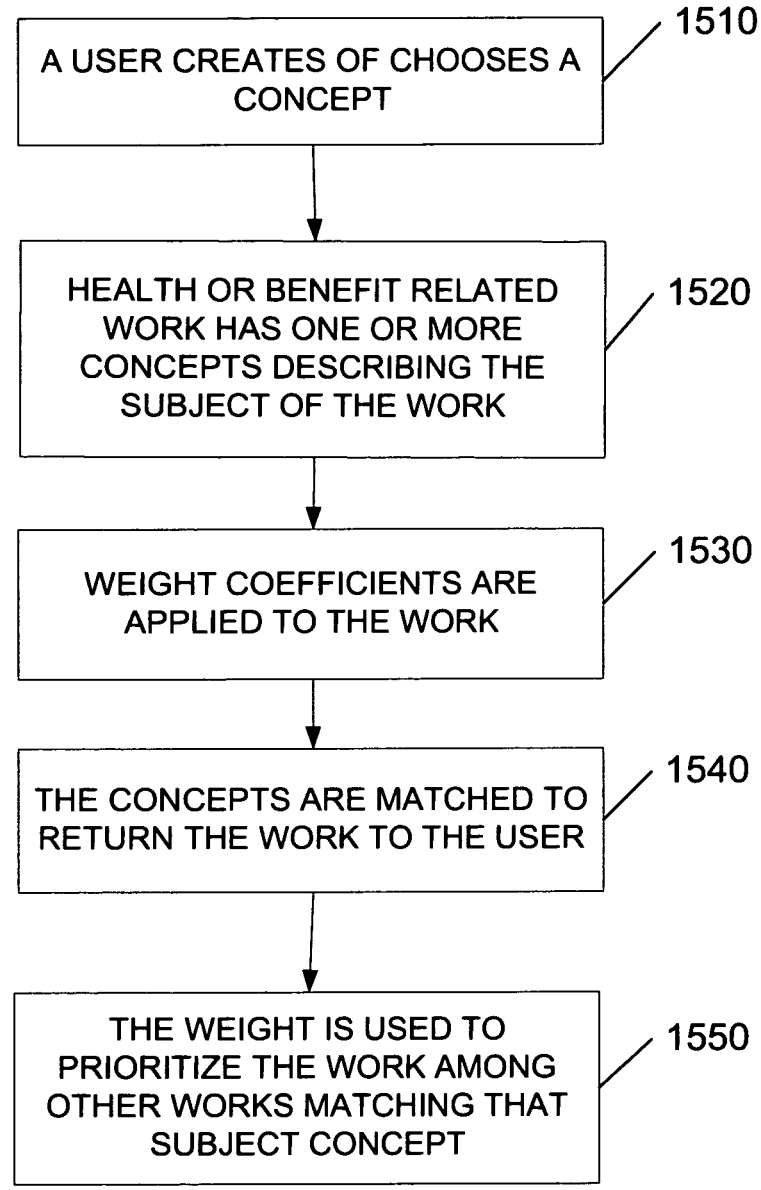

In one implementation of the system, a user may utilize user interface 110 to search the server 106 using concept identifiers for information on particular medical condition having interest to the user. One example of this process is illustrate in FIG. 15. In step 1510, enters a health or benefit-benefit related concept or chooses one or more concepts displayed in the user interface 110. As described above, the system maintains a collection of health or benefit-related works and the associated concepts describing the subject of the work, as shown in step 1520. Each work has a weight coefficient associated therewith to indicate such factors as recency, relevancy and importance of the work, as shown in step 1530. In step 1540, the user search concept is matched to the concepts available on the system and the associated works or summaries thereof are displayed to the user. As shown in step 1550, the displayed works are prioritized based on its weight coefficient.

In another implementation of the system, the server 106 may create and maintain one or more user profiles 107. The user profile can be implemented as a data structure stored in a non-volatile memory of server 106 or the like. The user profile may contain all information for the user, which includes both medical and non-medical information. The profile may be periodically updated to reflect actions taken by the user, including opening articles or tools.

An exemplary user profile data structure 107 is shown in FIG. 7. The user profile 107 may contain for each user information collected from the user such as user interests, answers to questions, health conditions, and medications. The user profile may also contain health or benefit-related concept associated with each user, such as Hearing Impaired and Elevated Cholesterol in Blood. The user profile may also contain the both taxonomically and semantically related health concepts. Thus, for example, for an Elevated Cholesterol Level condition, parent concepts include Elevated Blood Fats, Disorder of Lipoprotein Storage and Metabolism, and Disorder of Lipoprotein and Lipid Metabolism. In addition, each health or benefit-related concept in the user profile may be designated by a concept-specific identifier and may also include a designator identifying concept type, such as allergy, condition, medication, etc. Finally, links to the health or benefit-related works associated with the concepts may also be stored in the user profile.

Information in the user profile data structure may be viewed by the system administrator and/or by the user in various ways. One view of the user profile data structure 107 is shown in FIG. 8. The exemplary profile shows a relational concept organization. In particular, the user profile lists the following health concepts: morphine, hearing impaired, elevated cholesterol in blood and farsighted. Each concept in turn has a list of related concepts. Thus, a Farsighted condition includes the following related concepts: Eye Sight Refraction and Accommodation disorder, Refraction Errors, and Vision Disorders concepts. Another view of the user profile 107 is shown in FIG. 9. The exemplary profile shows alphabetical organization of all concepts associated with the user, as well as all the related concepts. There are, of course, numerous ways to display data stored in the user profile data structure that are within the scope of the present invention.

Figure 13:
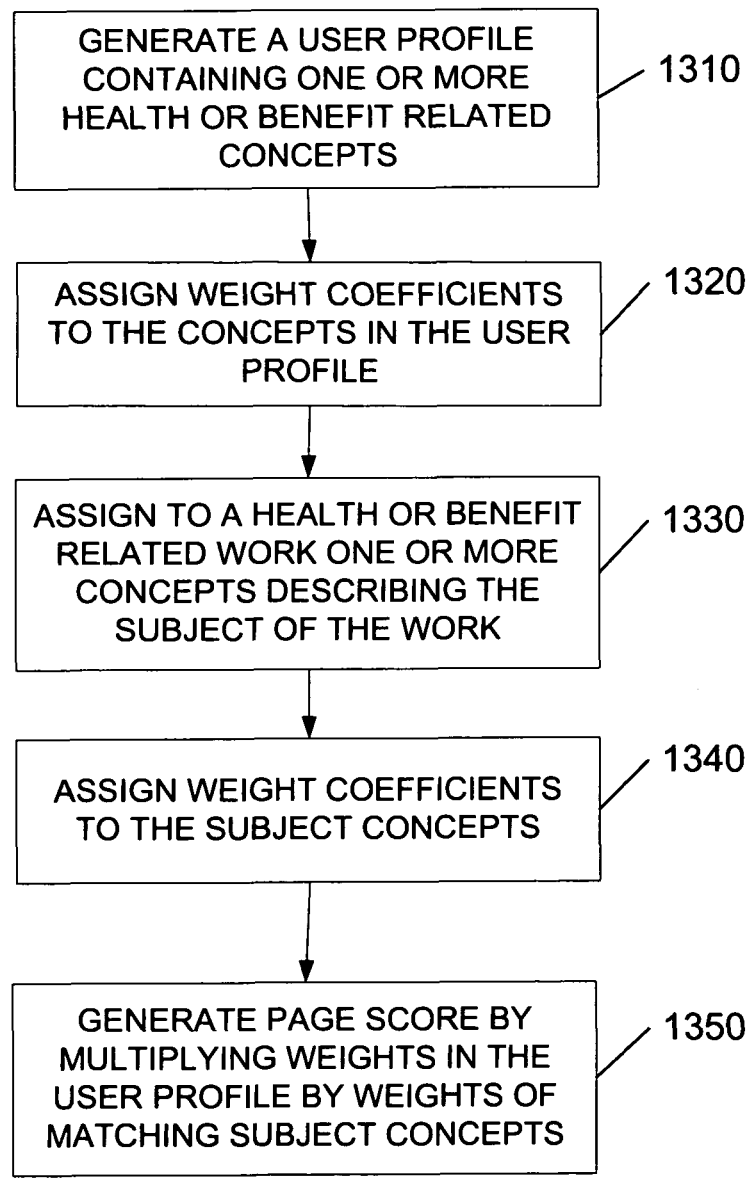

The user profiles may by generated in various ways. One example is illustrated in FIG. 13. As shown in step 1310, a user or a system administrator may create and populate a user profile with one or more health or benefit related concepts. In step 1320, weight coefficients may be assigned to the concepts in the user profile based on such factors as importance, recency and source of the concept. As shown in step 1330, all health benefit-related works have associated therewith one or more concepts describing the subject of the work. In step 1340, weight coefficients may be assigned to the subject concepts. Finally in step 1350, page scores may be generated by multiplying weights of the concepts in the user profile by weights of the matching subject concepts.

As shown in FIGS. 7, 8 and 9, the user profile data structure may also contain a weight coefficient field associated with each health or benefit-related concept. In one embodiment of the invention, a weight coefficient may be assigned to a concept by the user and/or by the system administrator to reflect relevance of that concept to the user. The weight coefficients may also be assigned based on one or more of the following criteria: imported current conditions, self-reported current condition, imported current medication, self-reported current medications, user's interests, user age or gender, and health plan or structure, etc. Thus, in one example, a value of such weight coefficient will be higher for those concepts reported by the user and in which the user expresses the greatest interest. Such a determination may be made, for example, by observing frequency of user access to health or benefit-related works associated with a particular concept. Similarly, the value of the weight coefficient will decrease if the user expresses very little or no interest in a particular health or benefit-related concept, and may eventually result in removal of such health or benefit-related concept from the user profile.

In one implementation of the system of the present invention, the weight coefficients may also be associated with the health or benefit-related works. In this case, a weight coefficient may indicate one or more of the following criteria: popularity of the health or benefit-related work, age of the health or benefit-related work, scope of the health or benefit-related work, and relevance of the health or benefit-related work. So, for example, for a user who identified himself as having "type 2 sugar disease," a recently published article on the subject of "adult-onset diabetes mellitus" will be give a higher weight coefficient than an old article on general subject of "diabetes." In addition, the value of the weight coefficient may be adjusted to reflect the popularity of the article among other users having similar interests. Thus, if the frequency of access to a particular article increases among users interested in the similar concepts, the weight coefficient of the article will also increase in the profiles of all users interested in the associated health or benefit-related concept. Furthermore, if the article is deemed to be important by the medical community, the weight coefficient assigned to the article will also be very high.

Figure 10:
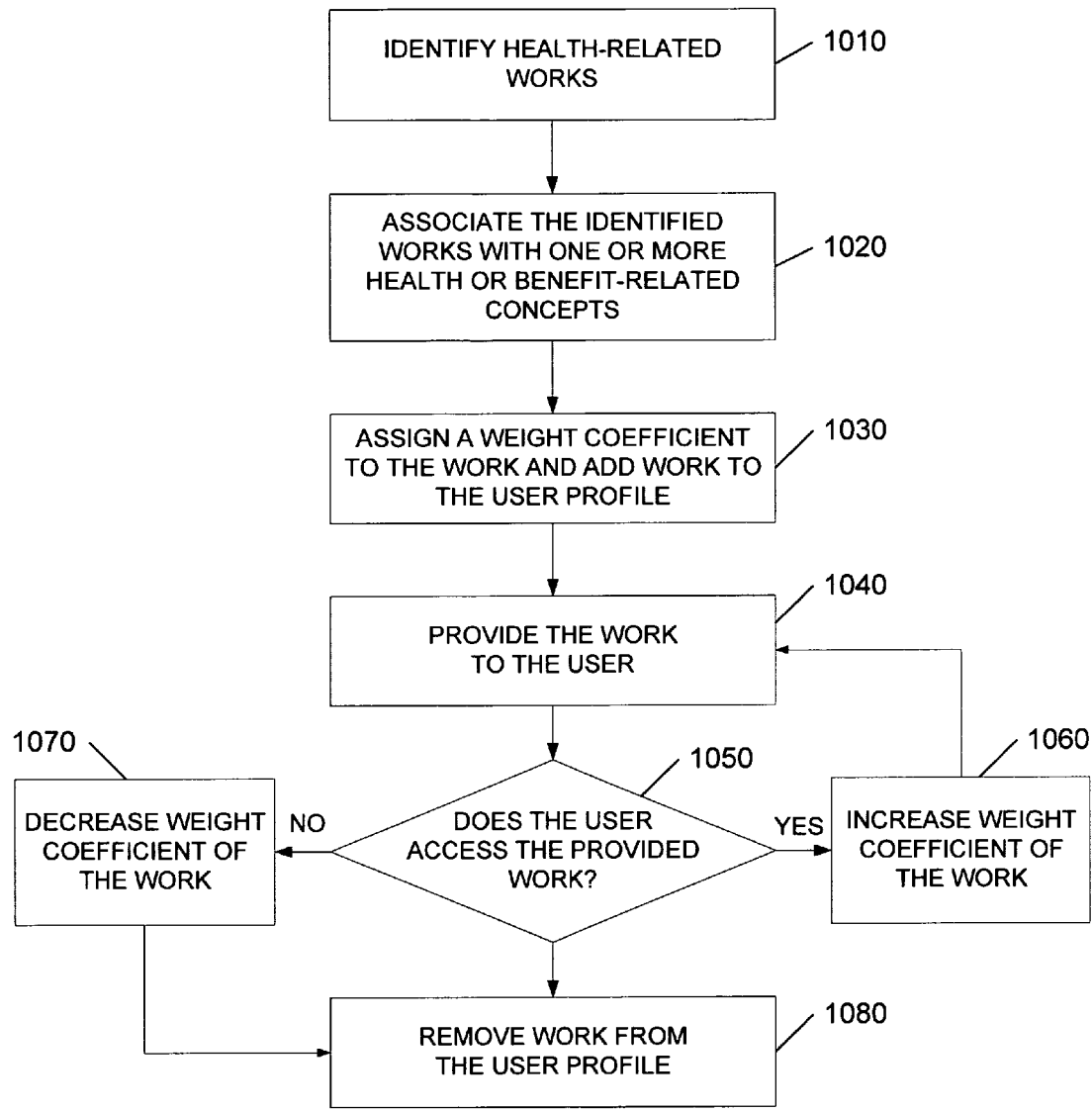
FIGS. 10-15 are flow diagrams of various implementation of health or benefit-related works personalization process.

One example of the above process is illustrated in more detail in FIG. 10. In step 1010, the system administrator identifies health or benefit-related works. The works are then associated in step 1020 with one or more health or benefit-related concepts provided by system. If there is no medical concept that fits the identified work, a new concept may be created by the administrator or the medical professional. Next, in step 1030, a weight coefficient is assigned to the health or benefit-related work and the reference link to the work is placed into the user profiles of the users interested in the associated concept. The value of the weight coefficient may be based on such factors as the scope of the work, how recent it is, eminence of its authors, etc. A link to the work is then provided to the user in step 1040. In step 1050, the system monitors frequency of access to the work by the users. If the work is frequently accessed by the system users, its weight coefficient is increased in step 1060, whereby the work takes priority over other works with lower weight coefficients and thus has a greater chance to be available to the users. If the work is accessed infrequently, or not at all, its weight coefficient is periodically decreased in step 1070, until its valued is 0 and the work is removed from the user profiles in step 1080.

In another implementation of the system, the combination of the weight coefficients of the health or benefit-related concepts and the associated health or benefit-related works, as well as other factors may be used to provide personalized works to the users. For example, in one implementation, the weight coefficient of a health or benefit-related concept may be multiplied by the weight coefficients of the health or benefit-related works associated with that concept to generate page scores for all works in the user profile. Page scores may then be ranked and only works with the highest page scores is displayed to the user. In another example, weight coefficient of a work may be multiplied by a time factor, which correlates to the age of the work. Therefore, as the weight coefficients of the health or benefit-related concepts and the associated health or benefit-related works change, or other factors such as age, popularity, etc. change, the respective page scores will also change and the works provided to the user will be dynamically updated.

One example of the above process is illustrated in FIG. 13. As shown in step 1310, a user or a system administrator may create and populate a user profile with one or more health or benefit related concepts. In step 1320, weight coefficients may be assigned to the concepts in the user profile based on such factors as importance, recency and source of the concept. As shown in step 1330, all health benefit-related works have associated therewith one or more concepts describing the subject of the work. In step 1340, weight coefficients may be assigned to the subject concepts. Finally in step 1350, by multiplying weights of the concepts in the user profile by weights of the matching subject concepts page scores may be generated. These page scores may determine order in which health and benefit-related works will be displayed to the user.

Figure 14:
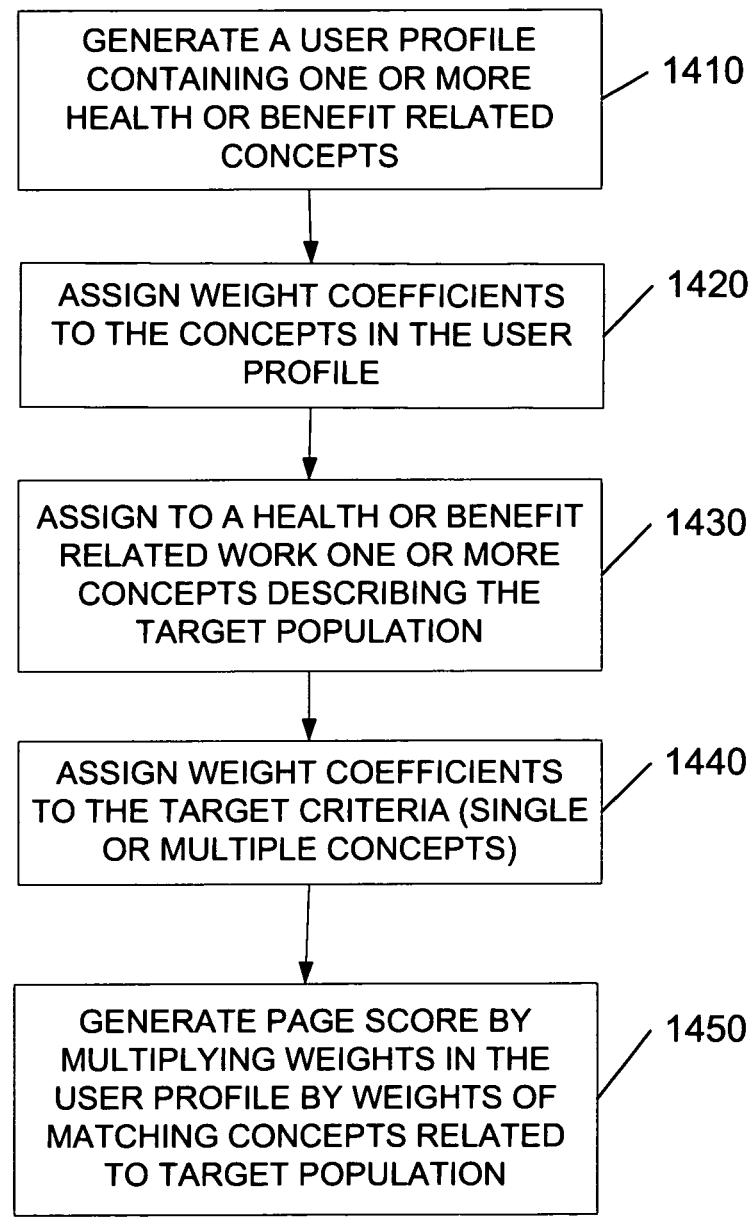

Another example of above process is illustrated in FIG. 14. As shown in step 1410, a user or a system administrator may create and populate a user profile with one or more health or benefit related concepts. In step 1420, weight coefficients may be assigned to the concepts in the user profile based on such factors as importance, recency and source of the concept. As shown in step 1430, concepts describing a target population of works is assigned to the health benefit-related works. In step 1440, weight coefficients may be assigned to one or more of these target population of works. Finally in step 1350, page scores may be generated by multiplying weights of the concepts in the user profile by weights of the matching concepts related to the target population of works. These page scores may determine order in which health and benefit-related works will be displayed to the user.

Figure 11:
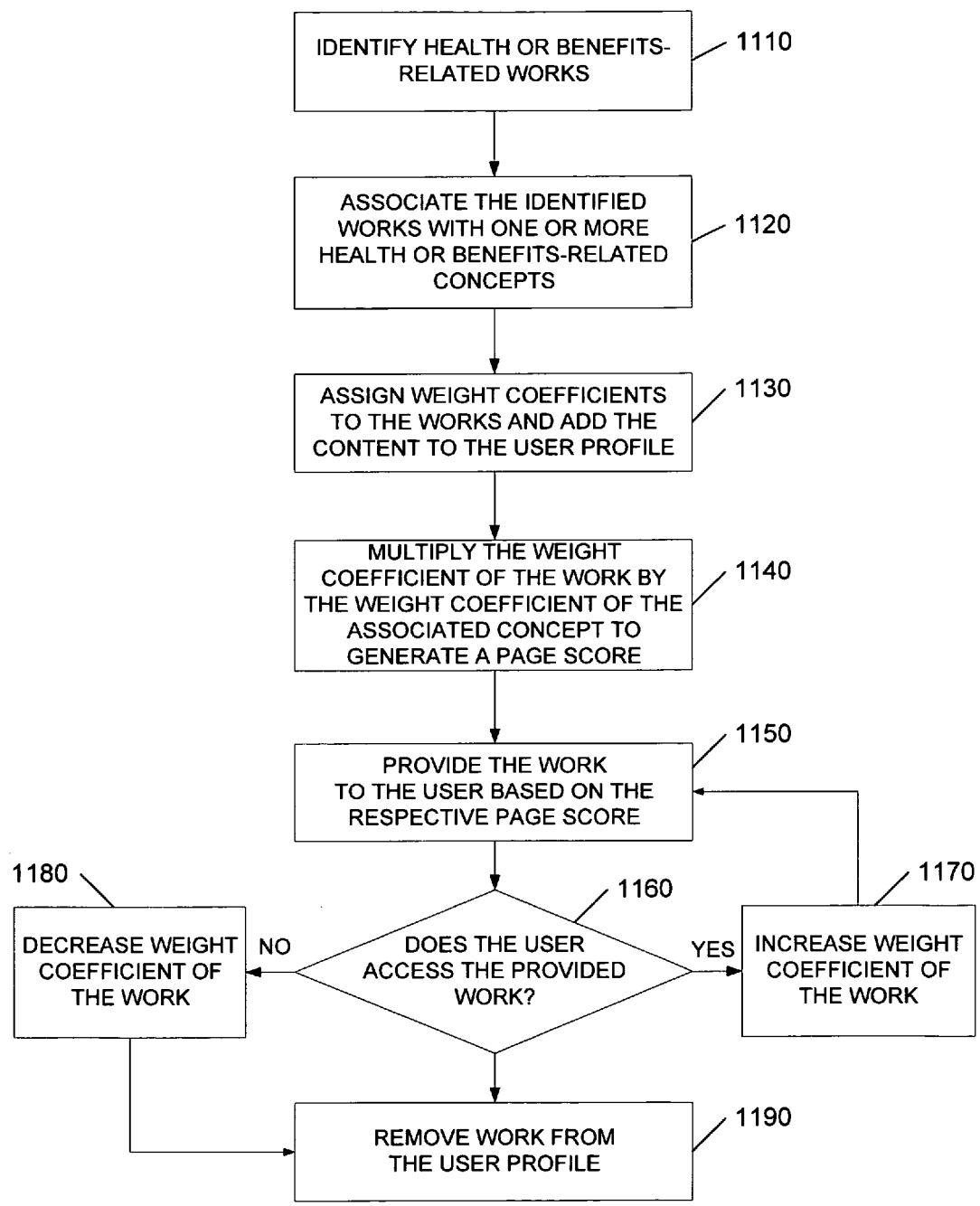

Another example of the above process is illustrated in more detail in FIG. 11. In step 1110, the system administrator identifies available health or benefit-related works. The works are then associated in step 1120 with one or more health or benefit-related concepts available on the system. If there is no medical concept that fits the identified works, a new concept may be created by the administrator or medical professional. Next, in step 1130, a weight coefficient is assigned to the identified health or benefit-related work and the link to the work is placed in user profiles of the users interested in the associated concept. In one implementation, the weight coefficient may further be adjusted to reflect age of the work. Thus, for example, the weight coefficient may be multiplied by a time factor, which is a variable that decrements with time. Then, in step 1140, coefficients of the work and the associated concept are multiplied to generate a page score. This page score may be used by the system to decide which work has a greater priority. A link to the work is then provided to the user in step 1150. In step 1160, the system monitors frequency of access to the work by the users. If the works is frequently accessed by the system users, its weight coefficient is increased in step 1170, whereby the subject work takes a priority over other works with lower weight coefficients and thus has a greater change of being available to the users. If the work is accessed infrequently, or not at all, its weight coefficient is periodically decreased in step 1180, until its valued is 0 and the work is removed from the user profiles in step 1190.

Figure 12:
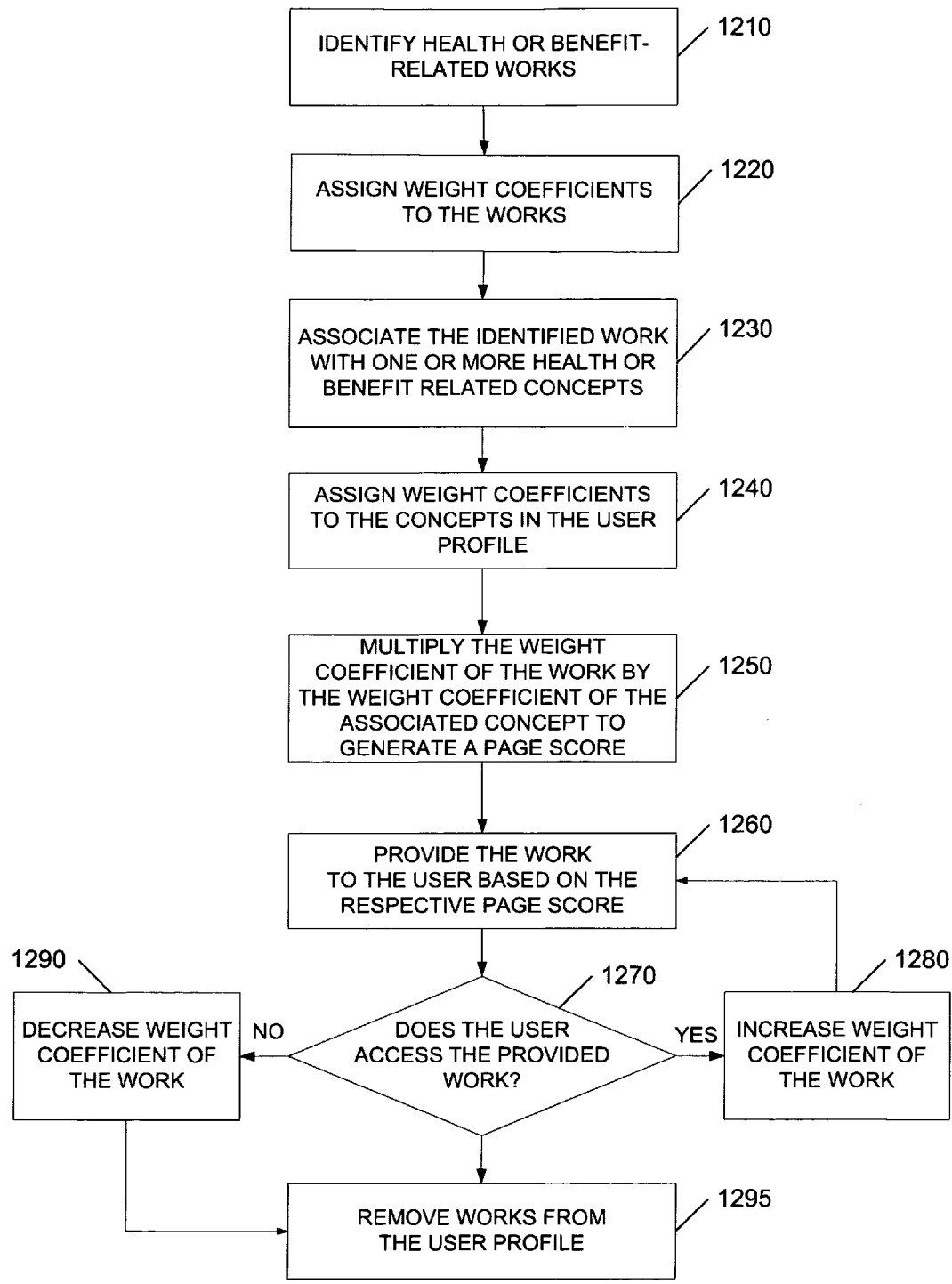

Yet another example of the above process is illustrated in more detail in FIG. 12. In steps 1210 and 1220, the system administrator identifies health or benefit-related works and assigns weight coefficients to the identified works. In step 1230, the administrator may associate the heath or benefit-related works with one or more health or benefit-related concepts. If there is no medical concept that fits the identified work, a new concept may be created by the administrator or medical professional. Next, in step 1240, weight coefficients are assigned to the health or benefit-related concepts in the user profiles and the associated work is linked to the concepts in the user profiles. Then, in step 1250, weight coefficients of the health or benefit-related concepts and the associated works are multiplied to generate page scores. Next, in step 1260, the work associated with particular health or benefit-related concepts is provided to the user based on the work's page score. The system then monitors in step 1270 the frequency of access by the user to the particular works and decreases or increases in steps 1280 or 1290 the weight coefficients of the work and/or concepts in response to the monitored frequency of access. When the weight coefficient of the particular work and/or concept falls below a particular threshold value, the work and/or concept is removed from the user profile.

FIGS. 16 and 17 show two exemplary views of user profile data structures having works organized using the above described weight coefficients and pages scores. In FIG. 16, various tools provided by system are organized according to their respective page scores. Thus, a Prostate Health Center tool, which is more popular and hence more frequently accessed by the users than, for example, an Eye Health Center tool, has a higher page score. In contrast, in FIG. 17, an article entitled "Drug Combo Improves Cholesterol Levels" has the highest weight coefficient of 32, however, since it is relatively old comparing to other articles, its weight coefficient is adjusted by time factor of 0.552, which brings its page score to 17.664, which is not the highest page score.

Figure 19:
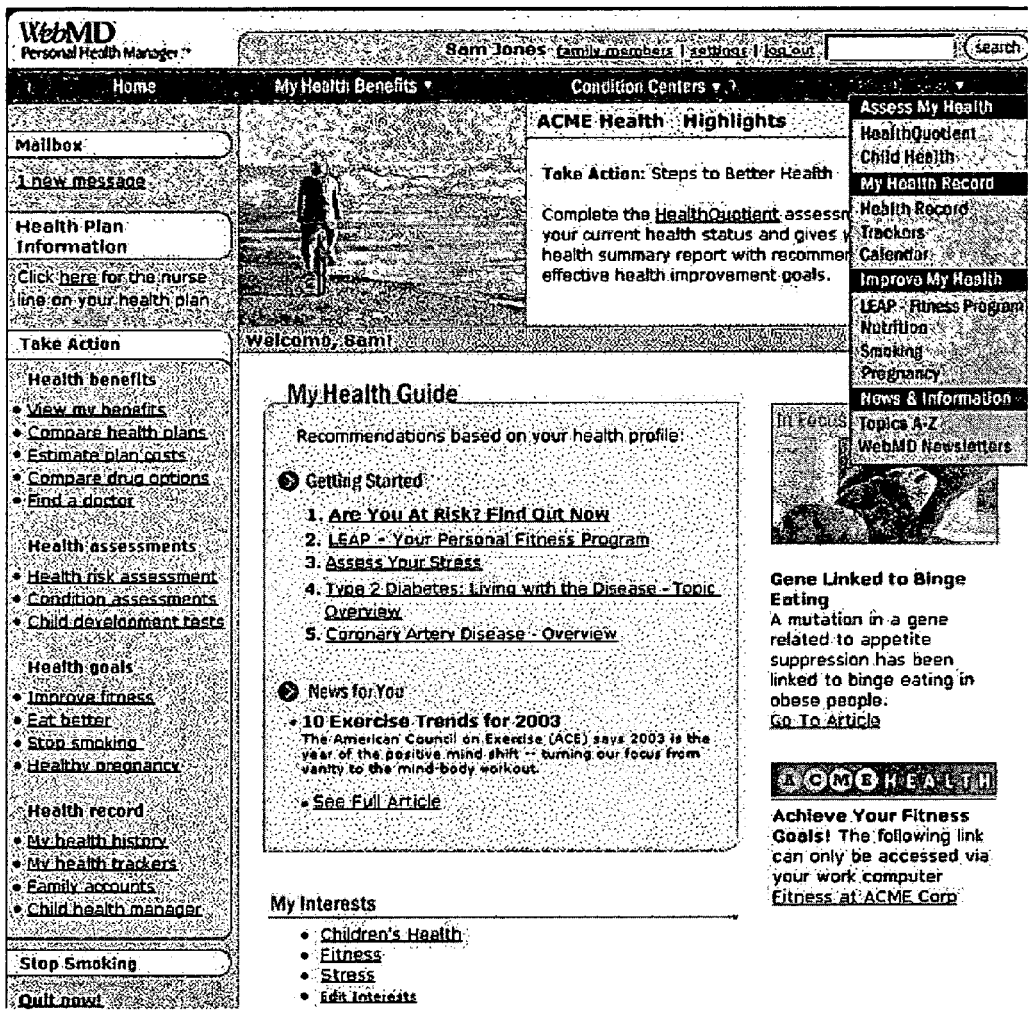
FIG. 19 is an exemplary personalized home page.

FIGS. 18 and 19 illustrate results of the above processes for personalizing health or benefit-related concepts and works. FIG. 18 shows exemplary results produced by the system of the present invention for search term "Trouble Breathing." The system associated the search terms with the general concept of "Asthma." The system also identified several taxonomically and semantically related concepts, including Exercise Induced Asthma, COPD, Allergies, Coughing and Pneumonia. Additional search results, including various related concepts and a number of associated health or benefit-related works, are shown in the Search Results pane. In addition, the system also provides several tools such as Asthma Assessment, Peak Flow Tracker, etc. These concepts and works were chosen primarily based on the associated weight coefficients and page scores, which in turn were computed base on the popularity of the work, its scope, age and various other factors.

FIG. 19 shows an exemplary home page of a system user, which is generated based on the above-described system of weight coefficients and page scores. The home page is generated from the information stored in the user profile data structure. Thus, when a user logs into the system, health or benefit-related concepts and works having the highest pages scores are retrieved from the user profile data structure and displayed to the user. In the present example, the user is provided with several tools and articles, which are displayed in My Health Guide pane. Also, based on the user interests, which are also typically specified in the user profile, such topics as Children's Health, Fitness, etc. are displayed to the user under My Interest category. In addition, various advertisements targeted to the user based on his profile may be displayed.

In one implementation of the system, each health or benefit-related work may have associated therewith several target attributes. These attributes may be used by the system to determine a user (or a group of users) who the subject health or benefit-related work targets. They may include gender of the targeted user, age of the targeted user, and one or more health or benefit-related concepts associated with the targeted user. In one example, target attributes for a health or benefit-related work may include male, age 40-60, history of prostate cancer, on the medicine Lupron, and on the medication Aspirin. The target attributes may also exclude certain users, such as those who are taking medication Proscar. As another example, a news article entitled "Exercise found to reduce the risk for breast cancer" and associated with concepts of breast cancer, breast cancer prevention, and exercise may be assigned target attributes of women between the ages of 70, and who are at risk for breast cancer, but who have not had a history of breast cancer. The target attributes may be stored in the user profile data structure as shown in FIGS. 16 and 17.

Figure 20:
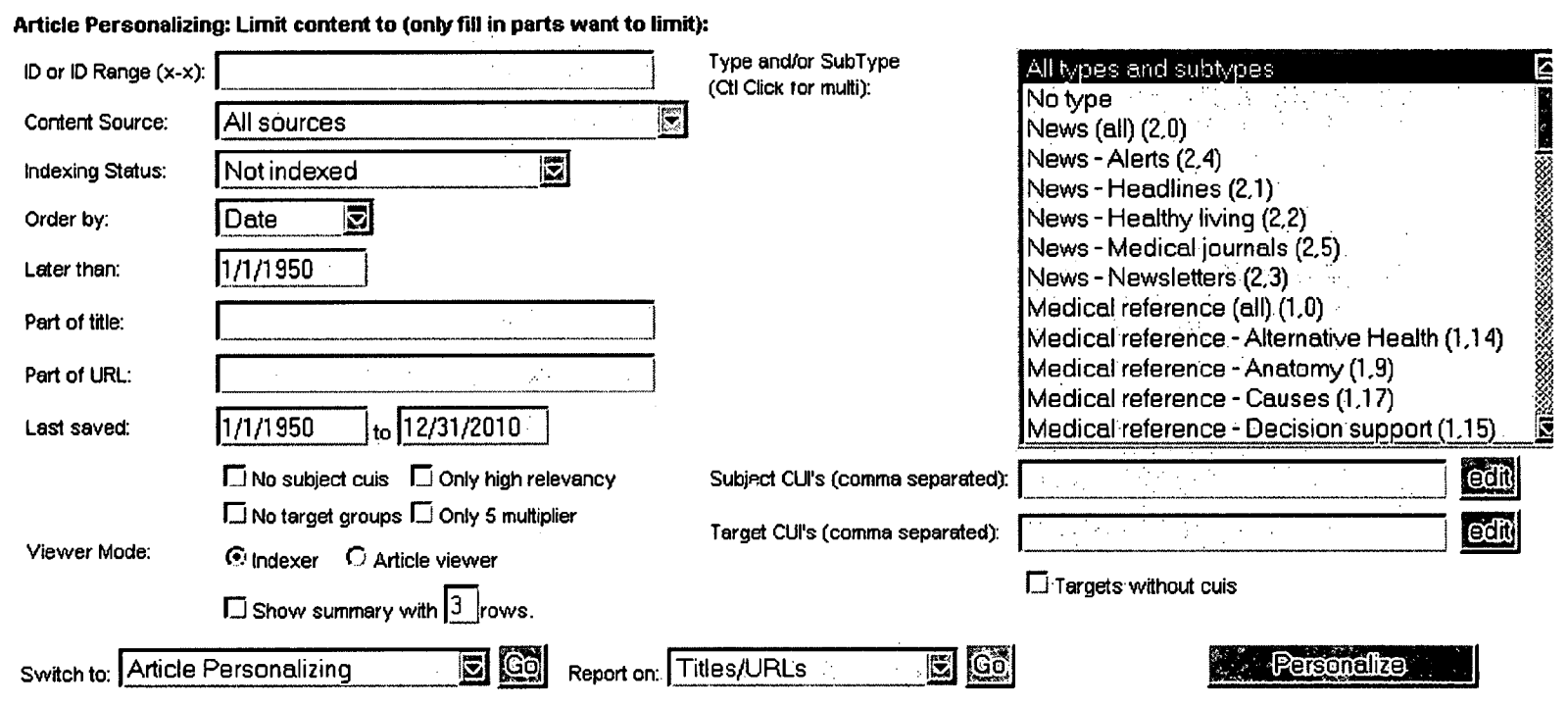
Figure 21:
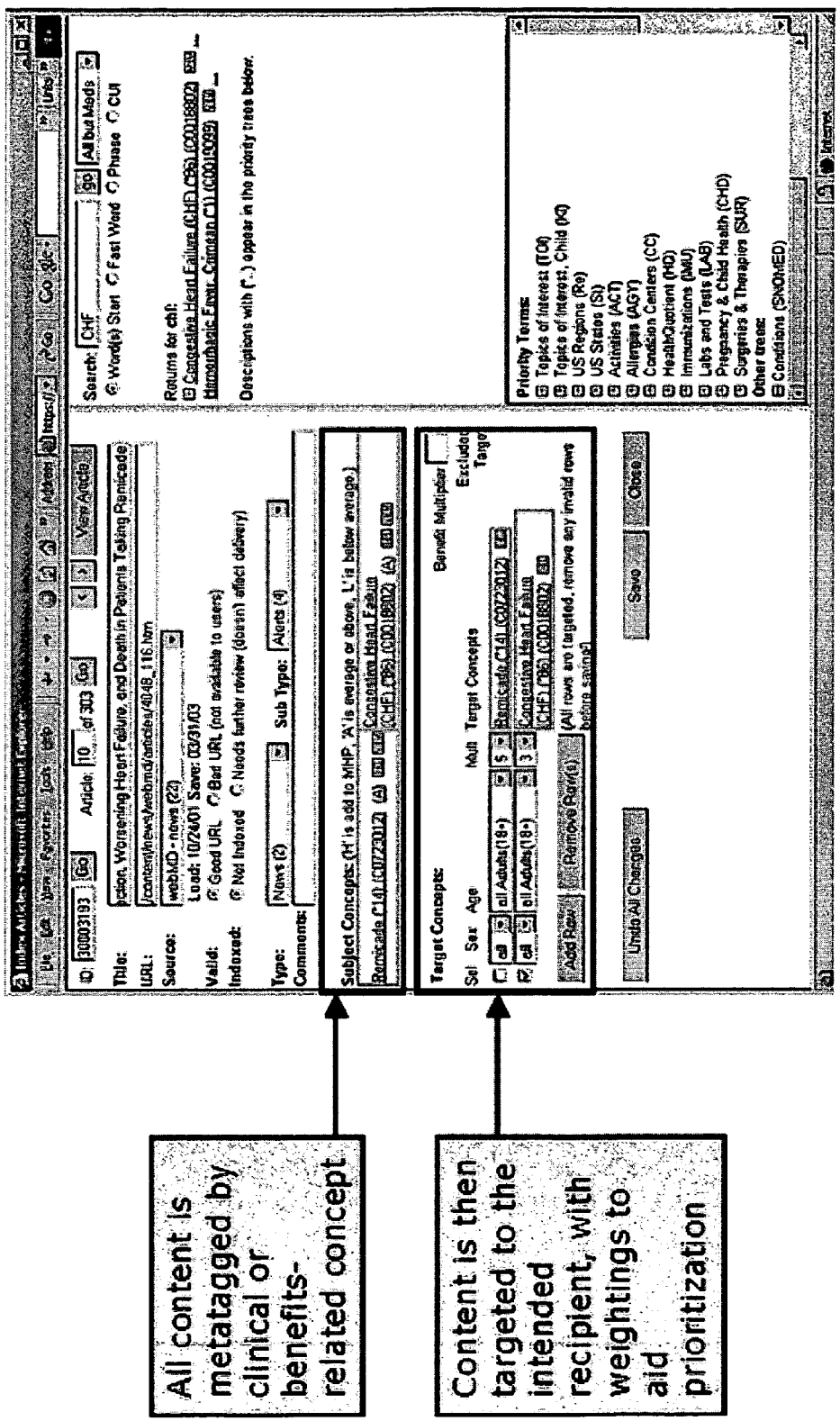
FIG. 21 is an exemplary works personalization tool.

FIGS. 20 and 21 show exemplary article indexing and personalization interfaces used by the system administrators or medical professionals to add new works to the system. First, with reference to FIG. 20, a new article is indexed. In one example, indexing may involve identifying source of the article and date when it was saved in the system. Also, during indexing, a concept-specific identifier may be assigned to the article and type and subtype of the article are specified. They type and subtype may include news, medical reference, advertisement, and the like. Second, with reference to FIG. 21, the article is personalized. In particular, the name and the URL of the article are entered into the system. The article is then associated with one or more health or benefit-related concepts. Next, weight coefficient and target attributes are specified, including gender, age, and target concept. The indexing and personalization processes are not limited to the above described steps and may have many other variations that are within the scope of the present invention.

Having described and illustrated the principles of the invention with reference to an illustrated embodiments, it will be recognized that the illustrated embodiments can be modified in arrangement and detail without departing from such principles. It should be understood that the programs, processes, or methods described herein are not related or limited to any particular type of computer apparatus, unless indicated otherwise. Various types of general purpose or specialized computer apparatus may be used with or perform operations in accordance with the teachings described herein. Elements of the illustrated embodiment shown in software may be implemented in hardware and vice versa.

In view of the many possible embodiments to which the principles of our invention may be applied, it should be recognized that the detailed embodiments are illustrative only and should not be taken as limiting the scope of our invention. Rather, we claim as our invention all such embodiments as may come within the scope and spirit of the following claims and equivalents thereto.

What is claimed is:

1. A computer-implemented method for providing personalized health or benefit-related works to a user, the method comprising:
 a. obtaining from the user, another information source, or both, personal health or benefit-related information comprising one or more health terms, each health term comprising at least one of a health-related term, a health-related code, a benefit-related term, and a benefit-related code;
 b. in a computer system, associating one or more of the obtained health terms with one or more health or benefit-related concepts;
 c. receiving from at least one of the user and a system administrator a first weight coefficient for each corresponding health or benefit-related concept based on the relevance of the corresponding health or benefit-related concept to the user;
 d. generating a user profile data structure for the user containing one or more of the associated health or benefit-related concepts and the first weight coefficients corresponding to the associated health or benefit-related concepts;

e. in the computer system, identifying a plurality of health or benefit-related works associated with the one or more health or benefit-related concepts;

f. the computer system assigning a second weight coefficient to each of the health or benefit-related works as a function of at least a degree to which the associated health or benefit-related concept describes a subject matter of the work upon receiving each of the health or benefit-related works;

g. providing the user computer network access to the plurality of health or benefit-related works, wherein the computer system provides said access based on a function of the first weight coefficients of the one or more health or benefit-related concepts and the second weight coefficients assigned to the plurality of health or benefit-related works; and h. adjusting the second weight coefficient assigned to at least one of the health or benefit-related works based on whether the user accesses the corresponding health or benefit-related work.

2. The method of claim 1, further comprising adjusting the second weight coefficient assigned to one of the health or benefit-related works based at least on one of popularity of the work, age of the work, importance of the work, and scope of the work.

3. The method of claim 1, further comprising storing in the user profile data structure links to the health or benefit-related works associated with the health or benefit-related concepts contained in the user profile data structure and the second weight coefficients assigned to the stored health or benefit-related works.

4. The method of claim 3, further comprising adjusting the second weight coefficient for one of the health or benefit-related works stored in the user profile data structure as a function of at least one of age and popularity of the health or benefit-related work.

5. A computer-implemented method for providing personalized health or benefit-related works to a user, the method comprising:

a. in a computer system, accessing a user profile data structure comprising one or more health or benefit-related concepts and first weight coefficients associated therewith indicating the relevance of the one or more concepts to the user, wherein the first weight coefficients are assigned by at least one of the user and a system administrator;

b. in the computer system, identifying a plurality of health or benefit-related works associated with the one or more health or benefit-related concepts;

c. the computer system assigning a second weight coefficient to each of the health or benefit-related works as a function of at least a degree to which the associated health or benefit-related concept describes a subject matter of the work upon receiving each of the health or benefit-related works;

d. providing the user computer network access to the plurality of health or benefit-related works, wherein the computer system provides said access based on a function of the first weight coefficients of the one or more health or benefit-related concepts and the second weight coefficients assigned to the plurality of health or benefit-related works; and e. adjusting the second weight coefficient assigned to at least one of the health or benefit-related works based on whether the user accesses the corresponding health or benefit-related work.

6. The method of claim 5, further comprising adjusting the second weight coefficient assigned to one of the health or benefit-related works based at least on one of popularity of the work, age of the work, importance of the work, and scope of the work.

7. The method of claim 6, further comprising storing in the user profile data structure links to the provided health or benefit-related works and the second weight coefficients associated therewith.

8. The method of claim 7, further comprising adjusting the second weight coefficient of one of the health or benefit-related works stored in the user profile data structure as a function of at least one of age and popularity of the health or benefit-related work.

9. The method of claim 7, further comprising adjusting the first weight coefficient of a health or benefit-related concept as a function of frequency of access by the user to the health or benefit-related works associated with the health or benefit-related concept.

10. A system for providing personalized health or benefit-related works to a user, the system comprising:

a. a non-transitory computer-readable medium having a user profile data structure stored thereon, wherein the user profile data structure comprises:

i. one or more health or benefit-related concepts, wherein each health or benefit-related concept has a first weight coefficient associated therewith indicating relevance of the health or benefit-related concept to the user, and wherein the first weight coefficient is assigned by at least one of the user and a system administrator, ii. links to a plurality of health or benefit-related works associated with the one or more health or benefit-related concepts, wherein each health or benefit-related work among the plurality of health or benefit-related works has a corresponding second weight coefficient assigned thereto; and b. a processor configured to:

i. assign the second weight coefficient to each of the health or benefit-related works as a function of at least a degree to which the associated health or benefit-related concept describes a subject matter of the work upon receiving each of the health or benefit-related works;

ii. access the user profile data structure and provide to the user computer network access to the plurality of the health or benefit-related works, the access being based on a function of the first weight coefficients of the health or benefit-related concepts and the second weight coefficients assigned to the plurality of health or benefit-related works; and iii. adjust the second weight coefficient assigned to at least one of the health or benefit-related works based on whether the user accesses the corresponding health or benefit-related work.

11. The system of claim 10, wherein the processor is further configured to adjust the second weight coefficient assigned to one of the health or benefit-related works based at least on one of popularity of the work, age of the work, importance of the work, and scope of the work.

12. The system of claim 10, wherein the processor is further configured to adjust the first weight coefficient of a health or benefit-related concept as a function of frequency of access by the user to the health or benefit-related works associated with the health or benefit-related concept.

13. The system of claim 10, wherein the processor is further configured to assign a unique identifier to each health or benefit-related concept and each health or benefit-related work stored in the user profile data structure.

14. A non-transitory computer-readable medium storing code for execution on a computer system, said code comprising instructions that, when executed by the computer system, cause the computer system to:
   a. define a user profile data structure comprising one or more health or benefit-related concepts and first weight coefficients associated therewith for indicating relevance of the health or benefit-related concepts to a user, wherein the first weight coefficients are assigned by at least one of the user and a system administrator;
   b. identify a plurality of health or benefit-related works associated with one or more health or benefit-related concepts;
   c. assign a second weight coefficient to each of the health or benefit-related works as a function of at least a degree to which the associated health or benefit-related concept describes a subject matter of the work upon receiving each of the health or benefit-related works;
   d. provide to the user computer network access to the plurality of health or benefit-related works, the access being based on a function of the first weight coefficients of the one or more health or benefit-related concepts and the second weight coefficients assigned to the plurality of health or benefit-related works; and
   e. adjust the second weight coefficient assigned to at least one of the health or benefit-related works based on whether the user accesses the corresponding health or benefit-related work.

15. The non-transitory computer-readable medium of claim 14, wherein the code further comprises instructions to cause the computer system to adjust the second weight coefficient assigned to one of the health or benefit-related works based at least on one of popularity of the work, age of the work, importance of the work, and scope of the work.

16. The non-transitory computer-readable medium of claim 14, wherein the code further comprises instructions to cause the computer system to store in the user profile data structure links to the provided health or benefit-related works and the second weight coefficients associated therewith.

17. The non-transitory computer-readable medium of claim 14, wherein the code further comprises instructions to cause the computer system to adjust the first weight coefficient of one of the health or benefit-related concepts as a function of frequency of access by the user to the health or benefit-related works associated with the health or benefit-related concept.

18. The non-transitory computer-readable medium of claim 14, wherein the code further comprises instructions to cause the computer system to categorize two or more health or benefit-related concepts in at least one of a taxonomic and a semantic relationship with each other.

19. The method of claim 1, wherein providing network access involves using both the first and second weight coefficients to rank the plurality of health or benefit-related works and presenting a list of the plurality of health or benefit-related works to the user in a rank order as determined by the first and second weight coefficients.

20. The method of claim 19, wherein using both the first and second weight coefficients to rank the plurality of health or benefit-related works involves multiplying the second weight coefficients by the first weight coefficients.

21. The method of claim 1, further comprising adjusting the second weight coefficient as a function of a measure of importance of the health or benefit-related work to a medical community.

22. The method of claim 1, further comprising adjusting the second weight coefficient as a function of a measure of the eminence of the authors of the health or benefit-related work.

23. The method of claim 5, wherein providing network access involves using both the first and second weight coefficients to rank the plurality of health or benefit-related works and presenting a list of the plurality of health or benefit-related works to the user in a rank order as determined by the first and second weight coefficients.

24. The method of claim 23, wherein using both the first and second weight coefficients to rank the plurality of health or benefit-related works involves multiplying the second weight coefficients by the first weight coefficients.

25. The system of claim 10, wherein the processor is further configured to provide network access by using both the first and second weight coefficients to rank the plurality of health or benefit-related works and present a list of the plurality of health or benefit-related works to the user in a rank order as determined by the first and second weight coefficients.

26. The system of claim 25, wherein the processor is further configured to use both the first and second weight coefficients to rank the plurality of health or benefit-related works by multiplying the second weight coefficients by the first weight coefficients.

27. The non-transitory computer readable medium of claim 14, wherein the code further comprises instructions to cause the computer system to use both the first and second weight coefficients to rank the plurality of health or benefit-related works and present a list of the plurality of health or benefit-related works to the user in a rank order as determined by the first and second weight coefficients.

28. The non-transitory computer readable medium of claim 27, wherein the instructions for using both the first and second weight coefficients to rank the plurality of health or benefit-related works includes instructions for multiplying the second weight coefficients by the first weight coefficients.

29. The method of claim 1, wherein the health or benefit-related works comprise at least one of health news, product and service information, information relating to health plan benefits, information relating to other benefits available to the user, disease information, medication information, articles, movie and audio clips, treatises, advertisements, other health-related content, and other benefit-related content.

30. The method of claim 5, wherein the health or benefit-related works comprise at least one of health news, product and service information, information relating to health plan benefits, information relating to other benefits available to the user, disease information, medication information, articles, movie and audio clips, treatises, advertisements, other health-related content, and other benefit-related content.

31. The system of claim 10, wherein the health or benefit-related works comprise at least one of health news, product and service information, information relating to health plan benefits, information relating to other benefits available to the user, disease information, medication information, articles, movie and audio clips, treatises, advertisements, other health-related content, and other benefit-related content.

32. The non-transitory computer-readable medium of claim 14, wherein the health or benefit-related works comprise at least one of health news, product and service information, information relating to health plan benefits, information relating to other benefits available to the user, disease information, medication information, articles, movie and audio clips, treatises, advertisements, other health-related content, and other benefit-related content.

* * * * *